(12) United States Patent
Cobbs et al.

(10) Patent No.: US 9,340,788 B2
(45) Date of Patent: *May 17, 2016

(54) PLATELET DERIVED GROWTH FACTOR RECEPTOR SUPPORTS CYTOMEGALOVIRUS INFECTIVITY

(71) Applicant: Sutter West Bay Hospitals, San Francisco, CA (US)

(72) Inventors: Charles Cobbs, San Francisco, CA (US); Liliana Soroceanu, San Francisco, CA (US)

(73) Assignee: Sutter West Bay Hospitals, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/887,244

(22) Filed: May 3, 2013

(65) Prior Publication Data

US 2014/0161811 A1    Jun. 12, 2014

Related U.S. Application Data

(62) Division of application No. 12/672,491, filed as application No. PCT/US2008/072540 on Aug. 7, 2008, now Pat. No. 8,435,510.

(60) Provisional application No. 60/954,612, filed on Aug. 8, 2007.

(51) Int. Cl.
| | | |
|---|---|---|
| G01N 33/574 | (2006.01) | |
| A61K 31/713 | (2006.01) | |
| C12N 15/113 | (2010.01) | |
| A61K 31/522 | (2006.01) | |
| A61K 31/662 | (2006.01) | |
| A61K 45/06 | (2006.01) | |
| C07K 16/28 | (2006.01) | |
| A61K 31/506 | (2006.01) | |
| A61K 39/395 | (2006.01) | |

(52) U.S. Cl.
CPC .......... *C12N 15/1137* (2013.01); *A61K 31/506* (2013.01); *A61K 31/522* (2013.01); *A61K 31/662* (2013.01); *A61K 31/713* (2013.01); *A61K 39/39558* (2013.01); *A61K 45/06* (2013.01); *C07K 16/2863* (2013.01); *C12N 15/1138* (2013.01); *C07K 2317/76* (2013.01); *C07K 2317/77* (2013.01); *C12N 2310/14* (2013.01)

(58) Field of Classification Search
USPC .......... 424/130.1, 142.1, 133.1, 141.1, 143.1; 435/6.1, 91.1, 91.31, 455; 514/1, 2, 44; 536/23.1, 24.5
See application file for complete search history.

(56) References Cited

U.S. PATENT DOCUMENTS

| | | | |
|---|---|---|---|
| 7,252,929 B2 | 8/2007 | Matsui et al. | |
| 8,435,510 B2 * | 5/2013 | Cobbs | A61K 31/522 424/130.1 |
| 2004/0082005 A1 * | 4/2004 | Cobbs | C12Q 1/6886 435/7.1 |
| 2005/0038080 A1 | 2/2005 | Boyer et al. | |
| 2006/0111423 A1 * | 5/2006 | Zeligs | 514/410 |
| 2006/0275260 A1 | 12/2006 | Riviere et al. | |
| 2007/0207974 A1 * | 9/2007 | Khvorova et al. | 514/44 |
| 2007/0265203 A1 | 11/2007 | Eriksson et al. | |
| 2008/0113351 A1 * | 5/2008 | Naito et al. | 435/6 |
| 2008/0194574 A1 * | 8/2008 | Eikhoff et al. | 514/252.11 |
| 2008/0213265 A1 | 9/2008 | Lanzavecchia et al. | |
| 2009/0110676 A1 * | 4/2009 | MacKay et al. | 424/130.1 |
| 2011/0150897 A1 * | 6/2011 | Meyer et al. | 424/158.1 |

FOREIGN PATENT DOCUMENTS

| | | |
|---|---|---|
| WO | 03/072704 A2 | 9/2003 |
| WO | 2005/048928 A2 | 6/2005 |
| WO | 2006/138729 A2 | 12/2006 |
| WO | 2007/038453 A2 | 4/2007 |

OTHER PUBLICATIONS

Johnson et al., J. Virology, vol. 75, No. 13, pp. 6022-6032 (2001).*
Valius et al., Cell, vol. 73, pp. 321-334 (1993).*
Di Pasquale et al., Nature Medicine, vol. 9, No. 10, pp. 1306-1312 (2003).*
Kapeller et al., Molecular and Cellular Biology, vol. 13, No. 10, pp. 6052-6063 (1993).*
Sequence Alignment Data.*
Cadena et al., "Receptor tyrosine kinases." FASEB J., 1992, vol. 6, pp. 2333-2337.
Young, Lee W., International Search Report and Written Opinion, PCT/US08/72540, United States Patent & Trademark Office, Jan. 27, 2009.
Cobbs et al., Modulation of Oncogenic Phenotype in Human Glioma Cells by Cytomegalovirus IE1-Mediated Mitogenicity, Cancer Res., Feb. 1, 2008, vol. 68, No. 3, pp. 724-730.
Cobbs et al., "Human cytomegalovirus induces cellular tyrosine kinase signaling and promotes glioma cell invasiveness," J. Neurooncol., 2007, vol. 85, pp. 271-280.
Soroceanu et al., "Platelet-derived growth factor—a receptor activation is required for human cytomegalovirus infection," Nature, Sep. 2008, vol. 455, pp. 391-396.
Nickitas-Etienne, Athina, International Preliminary Report on Patentability & Written Opinion, Date of Issuance of Report: Feb. 9, 2010, International Application No. PCT/US2008/07540.
McGary et al., "Imatinib Mesylate Inhibits Platelet-Derived Growth Factor Receptor Phosphorylation of Melanoma Cells but Does Not Affect Tumorigenicity In Vivo," J. Invest. Dermatol., 122(2):400-405, 2004.

* cited by examiner

*Primary Examiner* — Jane Zara
(74) *Attorney, Agent, or Firm* — Joseph R. Baker, Jr.; Gavrilovich, Dodd & Lindsey LLP

(57) ABSTRACT

The disclosure relates generally to compositions and methods useful for inhibiting the infection and propagation of viral particles, particularly members of the Herpesviridae family, and more particularly to cytomegalovirus (CMV).

11 Claims, 15 Drawing Sheets

HUVEC

PLATELET DERIVED GROWTH FACTOR RECEPTOR SUPPORTS CYTOMEGALOVIRUS INFECTIVITY

CROSS REFERENCE TO RELATED APPLICATIONS

This application is a divisional of U.S. application Ser. No. 12/672,491, filed Feb. 5, 2010, which is a U.S. National Stage Application filed under 35 U.S.C. §371 based upon International Application No. PCT/US08/72540, filed Aug. 7, 2008, which claims priority from U.S. Provisional Application Ser. No. 60/954,612, filed Aug. 8, 2007, the disclosures of which are incorporated herein by reference.

TECHNICAL FIELD

The disclosure relates generally to compositions and methods useful for inhibiting the infection and propagation of viral particles, particularly members of the Herpesviridae family, and more particularly to Cytomegalovirus (CMV).

BACKGROUND

Cytomegalovirus (CMV) is a member of Betaherpesvirinae in the subfamily Herpesviridae. CMV infects over 70% of the world's adult population and is the most common cause of congenital central nervous system (CNS) infection in humans. Clinically significant CMV disease frequently develops in patients immunocompromised by Human Immunodeficiency Virus (HIV), solid-organ transplantation, and bone-marrow transplantation. Additionally, congenital transmission from a mother with acute infection during pregnancy is a significant cause of neurological abnormalities and deafness in newborns.

Symptomatic disease in immunocompromised individuals can affect almost every organ of the body, resulting in fever of unknown origin, pneumonia, hepatitis, encephalitis, myelitis, colitis, uveitis, retinitis, and neuropathy. CMV establishes a latent infection in the host and may reactivate during a period of immunosuppression secondary to drugs or intercurrent infection.

In its latent state, the virus is known to reside in stem cells of the myeloid lineage and immune activation and differentiation of these cells can induce viral reactivation and replication. Stem cell populations in other organ systems are also likely to harbor persistent latent infection. Cellular differentiation state is tightly linked to viral expression patterns and this is thought to be due to differentiation-dependent chromatin remodeling of the viral major immediate-early (IE) promoter.

Additionally, association of CMV with several malignancies has been reported, including brain, breast, and colon cancers. A study has confirmed that CMV nucleic acids and proteins are detectable in over 90% of malignant gliomas. Furthermore, a significant proportion of these patients had detectable CMV in the peripheral blood, indicating the presence of an active viral infection.

Current treatment options for eradicating CMV infection includes antiviral agents such as Ganciclovir (a nucleoside analogue that inhibits DNA synthesis), Foscarnet (a DNA chain inhibitor of phosphorylation), Cidofovir (a nucleotide that inhibits DNA replication).

SUMMARY

The disclosure provides a method of treating or preventing a disease in which CMV is implicated in a subject, the method comprising administering a therapeutically effective amount of an agent that inhibits the activation of a platelet derived growth factor receptor (PDGF-R). In one embodiment, the agent is an antibody that binds to a glycoprotein B. In another embodiment, the agent is a small molecule inhibitor that inhibits that activity of a tyrosine kinase. In yet another embodiment, the agent inhibits the activation of a PDGFR-α receptor. In further embodiment, the disease is a neoplasm of brain, breast, or colon. The agent can be delivered by any number of methods and formulations including orally, parenterally, or by expression of transfected genetic material in vivo. The agent can be administered by a transmucosal, subcutaneous, transcutaneous, intramuscular, intravenous, intraocular delivery or implantation of sustained release formulations. In yet another embodiment, the method comprises a combination therapy comprising an active agent as mentioned above and further described herein and, for example, An antiviral agent or an antisense agent that inhibits expression of a gene of CMV. In one embodiment, the antiviral agent is ganciclovir or foscarnet.

The disclosure also provides a method of treating or preventing a disease in which CMV is implicated in a subject, comprising administering to a subject a therapeutically effective amount of a composition comprising an agent that modulates the expression and/or activity of a PDGF protein. In one embodiment, the agent comprises an inhibitory nucleic acid molecule that inhibits the expression of a PDGFR (e.g., an siRNA molecule). In yet another embodiment, the agent specifically inhibits the expression of PDGFRα. In a further embodiment, the agent is a small molecule inhibitor that inhibits that activity of a tyrosine kinase. As mentioned herein the disease can be a CMV-associated disease or disorder (e.g., a neoplasm of brain, breast, or colon a congenital CMV infection, perinatal CMV infection, immunocompetent patient CMV infection, CMV mononucleosis, post-transfusion CMV infection, immunocompromised CMV infection, CMV pneumoniti, CMV GI disease and CMV retinitis.

The disclosure also provides a composition comprising an agent selected from the group consisting of (i) a PDGFR inhibitor and (ii) an antiviral or an anti-CMV agent. The composition can comprise one or more carriers. In one embodiment, the PDGFR inhibitor comprises a kinase inhibitor (e.g., imatinib). In another embodiment, the PDGFR inhibitor specifically binds to a PDGFRα and prevents interaction of the receptor with its ligand. In yet another embodiment, the agent is an inhibitory nucleic acid. The composition can comprise a PDGFR inhibitor selected from the group consisting of a kinase inhibitor, an anti-PDGFR antibody, an inhibitory nucleic acid specific for a PDGFR or any combination thereof.

The disclosure also provides a method of inhibiting HCMV infection comprising contacting a subject with a glycoprotein B binding agent sufficient to reduce or inhibit the interaction of a glycoprotein B with a PDGFRα receptor.

The disclosure provides a method of inhibiting HCMV infection comprising contacting a subject with an agent that inhibits a phosphoinositide-3-kinase.

The disclosure further provides a method of inhibiting HCMV infection comprising contacting a subject with an agent that inhibits interaction of an HCMV with a platelet derived growth factor-α receptor (PDGFRα).

The disclosure provides a method of inhibiting HCMV infection comprising contacting a subject with an agent that specifically interacts with a PDGFRα receptor and inhibits PDGFRα from interacting with a CMV viral particle.

Also provided are methods of treating or preventing a disease in which CMV is implicated in a subject. The methods include administering to a subject in need of such treatment or prevention a therapeutically effective amount of a composition comprising an agent that modulates the expression and/or activity of a PDGF protein.

Also provided are kits for treating or preventing a disease in which CMV is implicated in a subject. A kit can include a therapeutically effective amount of a PDGF-R inhibiting species and instructions for systemic administration of the PDGF-R inhibiting species to the subject.

DETAILED DESCRIPTION

Figure 1:
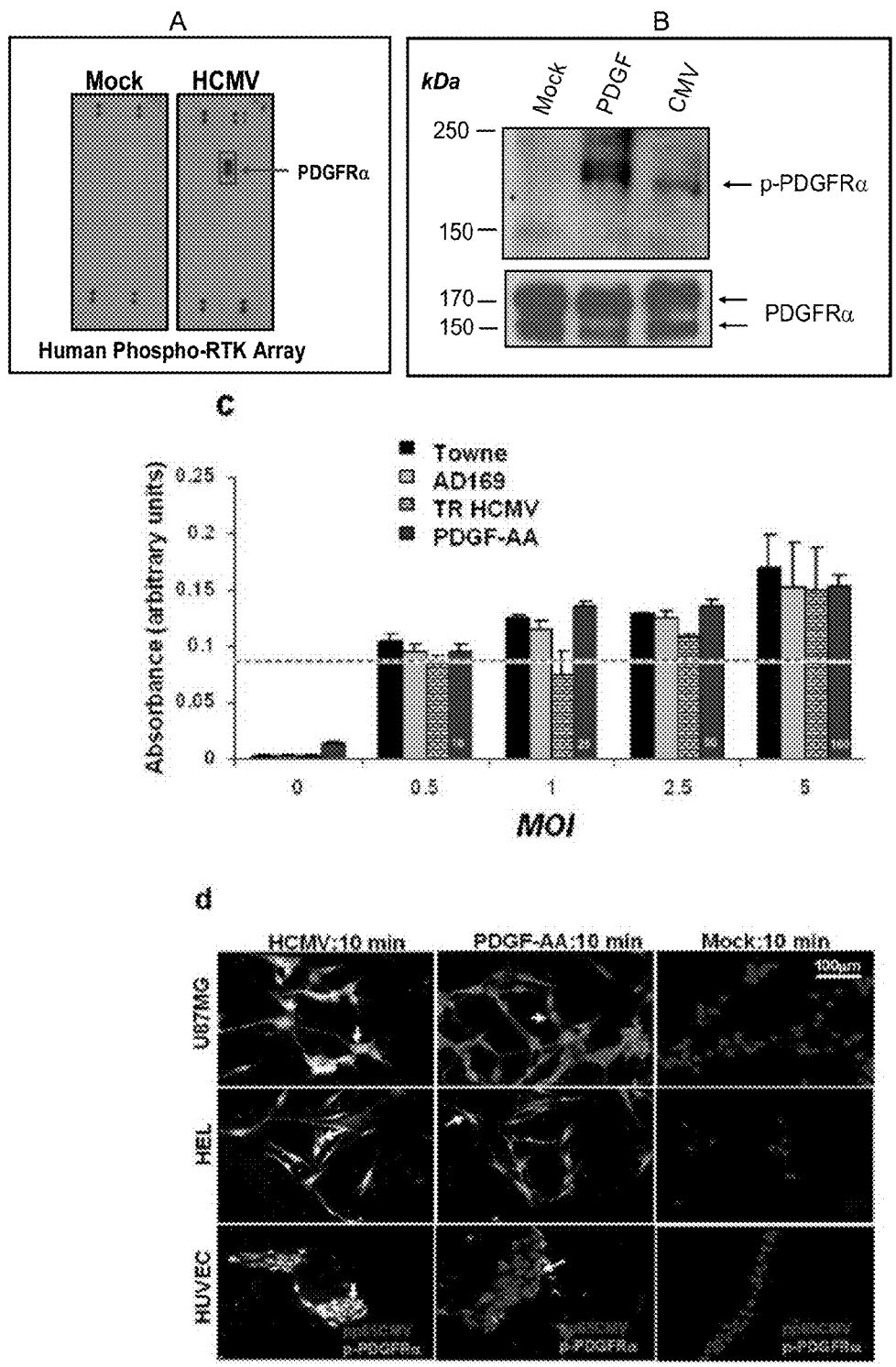
FIG. 1A-D shows that HCMV induces tyrosine phosphorylation of hPDGFRα. (A) Lysates of mock or HCMV treated cells were hybridized to a human phospho-RTK array. HCMV phosphorylates PDGFRα (arrow). (B) Western blot of HEL stimulated with mock, HCMV, or PDGF-AA, with indicated antibodies. (C) Phospho-PDGFRα specific ELISA of HEL stimulated with indicated HCMV strains and PDGF-AA (dotted line corresponds to 4000 pg/ml phospho-PDG-FRα). Mean absorbance values (n=6)±S.D are shown. (D) Immunofluorescence of pp65 and phospho-PDGFRα in indicated cells stimulated with mock, HCMV, or PDGF. Nuclei are stained with DAPI.

As used herein and in the appended claims, the singular forms "a," "and," and "the" include plural referents unless the context clearly dictates otherwise. Thus, for example, reference to "a cell" includes a plurality of such cells and reference to "the viral particle" includes reference to one or more viral particles known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of:"

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The publications herein are provided solely for their disclosure prior to the filing date of the present application. Nothing herein is to be construed as an admission that the inventors are not entitled to antedate such disclosure by virtue of prior disclosure.

Human cytomegalovirus (HCMV) is a ubiquitous human herpesvirus that can cause life threatening disease in the fetus and the immunocompromised host. Upon attachment to the cell, the virus induces robust inflammatory, interferon- and growth factor-like signaling. This disclosure demonstrates that platelet derived growth factor-α receptor (PDGFRα) is specifically phosphorylated by both laboratory and clinical isolates of HCMV in various human cell types, resulting in activation of the phosphoinositide-3-kinase (PI3-K) signaling pathway. Upon stimulation by HCMV, tyrosine phosphorylated PDGFRα associated with the p85 regulatory subunit of PI3-K and induced Akt phosphorylation, similar to the genuine ligand, PDGF-AA. Cells in which PDGFRα was genetically deleted or functionally blocked were non-permissive to HCMV entry, viral gene expression, or infectious virus production. Re-introducing human PDGFRα gene into knockout cells restored susceptibility to viral entry and essential viral gene expression. Blockade of receptor function with a humanized PDGFRα blocking antibody (e.g., IMC-3G3) or targeted inhibition of its kinase activity with a small molecule (e.g., Gleevec®) completely inhibited HCMV viral internalization and gene expression in human epithelial, endothelial, and fibroblast cells. Viral entry in cells harboring endogenous PDGFRα was competitively inhibited by pre-treatment with PDGF-AA. The disclosure further demonstrate that HCMV glycoprotein B (gB) directly interacts with PDGFRα, resulting in receptor tyrosine phosphorylation, and that gB neutralizing antibodies inhibit HCMV-induced PDGFRα phosphorylation.

Human herpesvirus 5 (human cytomegalovirus; HCMV) is ubiquitous worldwide, and persistent infection occurs in over 70% of adults. Association of HCMV infection with several human malignancies, including brain, prostate, and colon cancer have been reported (Harkins et al., 2002), suggesting a potential role for HCMV in oncogenesis.

HCMV is present in over 90% of human malignant gliomas, while no viral gene products were detectable in the non-malignant brain tissue. These findings have important implications for glioma biology, since accumulating evidence indicates that HCMV viral gene products can alter signaling pathways underlying cellular apoptosis, proliferation, migration, and transformation. For example, transcriptional activation of cellular oncogenes, including c-FOS, c-MYC and c-JUN are induced by HCMV exposure, reminiscent of growth factor-mediated signaling events. This activation does not require viral infectivity nor de novo viral protein synthesis.

In addition, HCMV infections are routinely encountered and increase morbidity and mortality in transplant patients and are associated with congenital CMV infection, perinatal CMV infection, immunocompetent patient, CMV mononucleosis, post-transfusion CMV—similar to CMV mononucleosis, immunocompromised patient (such as HIV patients), CMV pneumonitis, CMV GI disease, and CMV retinitis. A CMV related disease or disorder includes cancers (e.g., brain, prostate and colon cancers); congenital CMV infections, perinatal CMV infections, immunocompetent patient CMV infections, CMV mononucleosis, post-transfusion CMV infections, immunocompromised CMV infections, CMV pneumonitis, CMV GI disease and CMV retinitis.

In efforts to exert cell cycle control and inhibit apoptosis, DNA viruses have acquired during evolution the capacity to subvert cellular signaling pathways, most notably by activation of the PI3-K/AKT axis, or interference with p53 and Rb cell cycle control functions (Cooray, 2004, O'Shea, 2005). For example, activation of the PI-3K/AKT pathway is central to the ability of human herpesvirus 4 (Epstein-Barr virus; EBV) to establish viral latency and to induce transformation of B cells and of the oropharyngeal epithelium, leading to nasopharyngeal carcinoma (Cooray, 2004, Dawson et al., 2003).

Following infection, CMV typically remains in a latent state within the cells. In immunocompromised or immunosuppressed patients, CMV reactivation can result in invasive CMV disease such as pneumonitis, esophagitis, encephalitis, hepatitis, pacreatitis, adrenalitis, esophagitis, gastritis, enteritis, colitis, and retinitis.

Platelet derived growth factor receptor (PDGFR) is classified as a receptor tyrosine kinase (RTK), a type of cell surface receptor. Upon activation by platelet derived growth factor (PDGF), these receptors dimerize, and are switched on by autophosphorylation of several sites on their cytosolic domains, which serve to mediate binding of cofactors and subsequently activate signal transduction.

PDGFR is a transmembrane receptor tyrosine kinase. Ligand binding to the receptor results in dimerization of two receptors generally leading to intermolecular phosphorylation of each receptor, commonly referred to as autophosphorylation or transphosphorylation, and activation of the receptor complex. PDGF, which is a ligand for PDGFR, is a dimeric protein having two polypeptide chains joined by disulfide bonds. PDGF proteins and their receptors (PDGFRs) are involved in regulation of embryonic development, cell proliferation, survival and migration of several cell types. PDGF has also been linked to several diseases such as atherosclerosis, fibrosis, and malignant diseases. The PDGFR consists of two isozymes alpha and beta.

Protein kinases play critical roles in the regulation of biochemical and morphological changes associated with cellular growth and division (D'Urso, G. et al. (1990) Science 250: 786-791; Birchmeier. C. et al. (1993) Bioessays 15: 185-189). They serve as growth factor receptors and signal transducers and have been implicated in cellular transformation and malignancy (Hunter, T. et al. (1992) Cell 70: 375-387; Posada, J. et al. (1992) Mol. Biol. Cell 3: 583-592; Hunter, T. et al. (1994) Cell 79: 573-582). For example, protein kinases have been shown to participate in the transmission of signals from growth-factor receptors (Sturgill, T. W. et al. (1988) Nature 344: 715-718; Gomez, N. et al. (1991) Nature 353: 170-173), control of entry of cells into mitosis (Nurse, P. (1990) Nature 344: 503-508; Maller, J. L. (1991) Curr. Opin. Cell Biol. 3: 269-275) and regulation of actin bundling (Husain-Chishti, A. et al. (1988) Nature 334: 718-721). Protein kinases can be divided into two main groups based on either amino acid sequence similarity or specificity for either serine/threonine or tyrosine residues. A small number of dual-specificity kinases are structurally like the serine/threonine-specific group. Kinases can be further sub-divided into families whose members share a higher degree of catalytic domain amino acid sequence identity and also have similar biochemical properties. Most protein kinase family members also share structural features outside the kinase domain that reflect their particular cellular roles. These include regulatory domains that control kinase activity or interaction with other proteins (Hanks, S. K. et al. (1988) Science 241: 42-52).

Tyrosine kinases are an integral part of growth factor receptors and are essential for the propagation of growth factor signal transduction leading to cellular proliferation, differentiation, and migration. Growth factor receptors are also known as receptor tyrosine kinases (RTKs). Receptor tyrosine kinases are enzymes which span the cell membrane and possess an extracellular binding domain for growth factors such as epidermal growth factor, a transmembrane domain, and an intracellular portion which functions as a kinase to phosphorylate specific tyrosine residues in proteins and hence to influence cell proliferation.

This disclosure demonstrates that HCMV infection leads to prompt induction of cellular tyrosine kinase signaling, including tyrosine phosphorylation of a ~180 kDa protein, associated with the p85 regulatory subunit of PI3-K, and distinct from EGFR. Additional oncomodulatory viral properties are supported by the data showing that short term HCMV exposure induced recruitment of PLCγ and FAK activation, while persistent HCMV infection promoted extracellular matrix-dependent migration of malignant glioma cells, but not normal astrocytes. Taken together, the data provide HCMV-induced signaling pathways that modulate glioma cell growth, survival, and invasiveness.

The disclosure comprising the interaction between CMV and PDGFR as described herein can be used in one or more of the following methods: (a) screening assays; (b) predictive medicine (e.g., diagnostic assays, prognostic assays, monitoring clinical trials, and pharmacogenetics); and (c) methods of treatment (e.g., therapeutic and prophylactic). The information provided herein can be used, for example, to identify an agent or molecule associated with the CMV viral coat that is involved in CMV recognition of the PDGF-alpha receptor. Once identified, the molecule can be used to design compounds, such as antibodies, that bind to the molecule(s) and inhibit CMV interactions with the PDGF receptor. In addition, the CMV-PDGF receptor interaction can be used to screen for drugs or compounds which modulate such interactions, as well as to treat disorders characterized by activation, or over-activation, of the PDGF receptor. For example, existing data indicate that HCMV is likely to persistently infect neural precursor stem cells (NPCs) within the adult human brain. These NPCs are sensitive to oncogenic transformation caused by DNA mutations and sustained oncogenic signaling such as PDGFRα activation. A CD133 positive tumor stem cell population exists within malignant gliomas which retains similar properties to these NPCs. HCMV gene expression is activated by NPC differentiation, and HCMV gene products can clearly dysregulate oncogenic signaling pathways in cells, promote self-renewal of neural stem cells, cause blockade of cellular differentiation programs, and induce DNA mutations. Multiple HCMV gene products have been detected in a high percentage of human gliomas in vivo.

Based on the association of CMV with PDGF-alpha receptor as identified herein, molecules that modulate this interaction can act as novel therapeutic agents for controlling one or more of cellular proliferative and/or differentiative disorders, disorders associated with bone metabolism, immune disorders, hematopoietic disorders, cardiovascular disorders, liver disorders, viral diseases, pain or metabolic disorders.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as those affecting the lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

Aberrant expression and/or activity of a PDGF-alpha kinase can mediate disorders associated with bone metabolism. "Bone metabolism" refers to direct or indirect effects in the formation or degeneration of bone structures, e.g., bone formation, bone resorption, etc., which can ultimately affect the concentrations in serum of calcium and phosphate. This term also includes activities mediated by PDGF alpha kinase effects in bone cells, e.g. osteoclasts and osteoblasts that can in turn result in bone formation and degeneration.

Exemplary immune disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. The diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) Crit. Rev. in Oncol./Hemotol. 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Additional examples of hematopoieitic disorders or diseases include, but are not limited to, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjögren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

Examples of disorders involving the heart or "cardiovascular disorder" include, but are not limited to, a disease, disorder, or state involving the cardiovascular system, e.g., the heart, the blood vessels, and/or the blood. A cardiovascular disorder can be caused by an imbalance in arterial pressure, a malfunction of the heart, or an occlusion of a blood vessel, e.g., by a thrombus. Examples of such disorders include hypertension, atherosclerosis, coronary artery spasm, congestive heart failure, coronary artery disease, valvular disease, arrhythmias, and cardiomyopathies.

Disorders which can be treated or diagnosed by methods described herein include, but are not limited to, disorders associated with an accumulation in the liver of fibrous tissue, such as that resulting from an imbalance between production and degradation of the extracellular matrix accompanied by the collapse and condensation of preexisting fibers. The methods described herein can be used to diagnose or treat hepatocellular necrosis or injury induced by a wide variety of agents including processes which disturb homeostasis, such as an inflammatory process, tissue damage resulting from toxic injury or altered hepatic blood flow, and infections (e.g., bacterial, viral and parasitic). For example, the methods can be used for the early detection of hepatic injury, such as portal hypertension or hepatic fibrosis. In addition, the methods can be employed to detect liver fibrosis attributed to inborn errors of metabolsim, for example, fibrosis resulting from a storage disorder such as Gaucher's disease (lipid abnormalities) or a glycogen storage disease, A1-antitrypsin deficiency; a disorder mediating the accumulation (e.g., storage) of an exogenous substance, for example, hemochromatosis (iron-overload syndrome) and copper storage diseases (Wilson's disease), disorders resulting in the accumulation of a toxic metabolite (e.g., tyrosinemia, fructosemia and galactosemia) and peroxisomal disorders (e.g., Zellweger syndrome). Additionally, the methods described herein are useful for the early detection and treatment of liver injury associated with the administration of various chemicals or drugs, such as for example, methotrexate, isonizaid, oxyphenisatin, methyldopa, chlorpromazine, tolbutamide or alcohol, or which represents a hepatic manifestation of a vascular disorder such as obstruction of either the intrahepatic or extrahepatic bile flow or an alteration in hepatic circulation resulting, for example, from chronic heart failure, veno-occlusive disease, portal vein thrombosis or Budd-Chiari syndrome.

Additionally, PDGFR-alpha tyrosine kinase play a role in the etiology of certain viral diseases including, but not limited to, Hepatitis B, Hepatitis C and Herpes Simplex Virus (HSV). Modulators of PDGFR-alpha kinase activity can be used to control viral diseases. The modulators can be used in the treatment and/or diagnosis of viral infected tissue or virus-associated tissue fibrosis, especially liver and liver fibrosis. Also, PDGFR-alpha kinase modulators can be used in the treatment and/or diagnosis of virus-associated carcinoma, glioma, and hepatocellular cancer.

Accordingly, the disclosure provides methods and compositions useful for treating HCMV infection and related diseases and disorders. For example, inhibition of tyrosine kinases activity, tyrosine phosphorylation of PI3-K-Akt, inhibition of PLCγ and FAK activation inhibition are useful for inhibiting HCMV activation and infectivity.

In addition, the disclosure provides cellular targets for CMV viral entry and infection of cells. Platelet derived growth factor receptor-alpha (PDGFR-α) expression and activation is required for CMV viral entry into cells.

This disclosure demonstrates that expression and activation of PDGFR is required for CMV infection and that such activation is associated with certain diseases, as discussed above. Accordingly, PDGFR-alpha activation antagonists can be used to prevent and to treat CMV infections and CMV-related diseases and diseases. This can be achieved by using agents that compete in an antagonistic manner with PDGF for receptor binding; receptor blocking agents and kinase inhibitors. A PDGFR activation antagonist thus includes an antibody that binds to and inhibits the interaction of a receptor ligand with its cognate; an antibody that binds to and inhibits the receptor binding domain; a small molecule kinase inhibitor; a soluble PDGF receptor domains; inhibitory nucleic acids (e.g., antisense siRNA and the like) that inhibit the expression of PDGFR (e.g., PDGFRα); and fragments of a ligand for a PDGF receptor that do not activate the receptor. As discussed more fully below such PDGF activation antagonists can be used alone or in combination with another antagonist. In one embodiment, the PDGF activation antagonist is specific for PDGFRα.

Several companies have developed therapeutic agents that target PDGFR-α including small molecule inhibitors and antibodies. For example, monoclonal antibodies that target PDGFR-alpha have been reported. International publication number WO 1992/013867 describes preparation of mouse or rabbit monoclonal and/or polyclonal antibodies to PDGF receptor constructs. International publication number WO 1995/000659 relates to a monoclonal antibody that specifically binds to PDGFR-alpha. International publication number WO2006/138729 discloses a human monoclonal antibody, termed 3G3 (ImClone Systems, Inc.), that targets PDGFR-alpha (the disclosures of the foregoing applications are incorporated herein by reference).

Various tyrosine kinase small molecule inhibitors and peptidomimetics can also be used in the methods and compositions of the disclosure. A number of tyrosine kinase inhibitors useful in the disclosure can be identified by one of skill in the art. For example, AZD2171; Dasatinib; Erlotinib; Gefitinib; Imatinib; Lapatinib; Nilotinib; Semaxanib; SGI-AXL-277 (a pyrrolopyrimidine) (SuperGen); Sunitinib; and Vandetanib. Other examples of tyrosine kinase inhibitors include: imatinib mesylate (Gleevec®) marketed by Novartis, IMC-3G3 (anti-PDGFR-α monoclonal antibody) developed by ImClone, sunitinib malate (Sutent®) developed by Pfizer, sorafenib tosylate (Nexavar®) marketed by Bayer, and Vatalanib (PTK787/ZK222584). In addition, Leflunomide (Arava®) is a small-molecule PDGFR tyrosine kinase inhibitor, and AG013736 (Axitinib®) by Pfizer is an imidazole derivative that inhibits the tyrosine kinase portion of all VEG-FRs and PDGFR-B. Axitinib (also known as AG013736; N-Methyl-2-[[3-[(E)-2-pyridin-2-ylethenyl]-1H-indazol-6-yl]sulfanyl]benzamide) is a small molecule tyrosine kinase inhibitor under development by Pfizer. Bosutinib (rINN/USAN; code named SKI-606; 4-[(2,4-dichloro-5-methoxyphenyl)amino]-6-methoxy-7-[3-(4-methylpiperazin-1-yl)propoxy]quinoline-3-carbonitrile) is a tyrosine kinase inhibitor being developed by Wyeth. Cediranib (tentative trade name Recentin; 4-[(4-fluoro-2-methyl-1H-indol-5-yl)oxy]-6-methoxy-7-[3-(pyrrolidin-1-yl)propoxy]quinazoline), also known as AZD2171, is a potent inhibitor of vascular endothelial growth factor (VEGF) receptor tyrosine kinases. Dasatinib, also known as BMS-354825 (N-(2-chloro-6-methylphenyl)-2-[[6-[4-(2-hydroxyethyl)-1-piperazinyl]-2-methyl-4-pyrimidinyl]amino]-5-thiazole carboxamide monohydrate), is a drug produced by Bristol-Myers Squibb and sold under the trade name Sprycel®. Dasatinib is an oral dual BCR/ABL and Src family tyrosine kinases inhibitor. Erlotinib hydrochloride (originally coded as OSI-774; N-(3-ethynylphenyl)-6,7-bis(2-methoxyethoxy)quinazolin-4-amine) is marketed in the United States by Genentech and OSI Pharmaceuticals and elsewhere by Roche under the tradename Tarceva®. Gefitinib (INN) (originally coded ZD1839; N-(3-chloro-4-fluoro-phenyl)-7-methoxy-6-(3-morpholin-4-ylpropoxy)quinazolin-4-amine is similar manner to erlotinib (marketed as Tarceva®). Gefitinib is marketed by AstraZeneca and Teva under the trade name Iressa®. Imatinib is currently marketed by Novartis as Gleevec® (USA) or Glivec® (Europe/Australia) as its mesylate salt, imatinib mesilate (INN). It was originally coded during development as CGP57148B or STI-571 (4-[(4-methylpiperazin-1-yl)methyl]-N-[4-methyl-3-[(4-pyridin-3-ylpyrimidin-2-yl)amino]-phenyl]-benzamide). Lapatinib (INN) or lapatinib ditosylate (USAN), also known as GW572016 (N-[3-chloro-4-[(3-fluorophenyl)methoxy]phenyl]-6-[5-[(2-methylsulfonylethylamino)methyl]-2-furyl]quinazolin-4-amine), is marketed by GSK under the tradename Tykerb® and Tyverb®. Lestaurtinib (rINN, codenamed CEP-701) is a tyrosine kinase inhibitor. Nilotinib, in the form of the hydrochloride monohydrate salt, is a tyrosine kinase inhibitor, also known by its clinical code AMN107 (4-methyl-N-[3-(4-methylimidazol-1-yl)-5-(trifluoromethyl)phenyl]-3-[(4-pyridin-3-ylpyrimidin-2-yl)amino]benzamide). Semaxanib (SU5416; (3Z)-3-[(3,5-dimethyl-1H-pyrrol-2-yl)methylidene]-1H-indol-2-one) is a tyrosine kinase inhibitor. Sorafenib tosylate (Nexavar®) marketed by Bayer. Sunitinib (marketed as Sutent®, and previously known as SU11248; N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide) is an oral, small-molecule, multi-targeted receptor tyrosine kinase (RTK) inhibitor. Vandetanib (also known as ZD6474; N-(4-bromo-2-fluoro-phenyl)-6-methoxy-7-[(1-methyl-4-piperidyl)methoxy]quinazolin-4-amine), is a tyrosine kinase inhibitor currently undergoing clinical trials. Vandetanib is being developed by AstraZeneca. Vatalanib (PTK787/ZK222584) a protein tyrosine kinase inhibitor being developed by Bayer. In addition, Leflunomide (Arava®) is a small-molecule PDGFR tyrosine kinase inhibitor; AZD2171; and SGI-AXL-277 (a pyrrolopyrimidine).

Commercially available PDGFR-α siRNA molecules are available from Santa Cruz Biotechnology and comprise individually or a pool of 20-25 nucleotide target-specific siRNAs designed to knock down gene expression. In another embodiment, the siRNA molecule can comprise a sequence selected from the group consisting of (5'→3'): CGAGACUCCU-GUAACCUUAUU (SEQ ID NO:1), GAGCUUCACCUAU-CAAGUUUU (SEQ ID NO:2), GACAGUGGCCA-UUAUACUAUU (SEQ ID NO:3), GAAUAGGGAUAGCUUCCUGUU (SEQ ID NO:4), and any combination thereof.

Compositions comprising one or more of the foregoing inhibitors are useful in treating CMV related diseases and disorders. For example, in one embodiment, a pharmaceutical composition comprising a tyrosine kinase inhibitor is useful for inhibiting or reducing the infection of or spread of a CMV. In yet another embodiment, a pharmaceutical composition comprising an antibody that binds to and inhibits the interaction of a PDGFR-alpha with its ligand is used. In yet another embodiment, an antisense or siRNA molecule can be used to reduce the expression of a PDGFR-alpha polypeptide. In yet a further embodiment, a combination of any of the foregoing can be used.

The identification of PDGFR as a factor in CMV infection provides for the use of "active compounds" (e.g., nucleic acid molecules, proteins, antibodies and small molecules) that modulate CMV-PDGFR interactions or activation in pharmaceutical compositions suitable for administration. Such compositions typically comprise the active compound and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. Such carriers can include porous silicon, $SiO_2$ and the like for delivery to the eye or as slow release carriers. The use of such media and agents for pharmaceutically active substances is well known in the art. Except insofar as any conventional media or agent is incompatible with the active compound, use thereof in the compositions is contemplated. Supplementary active compounds or combinations of active compound can also be incorporated into the compositions. As used herein an active compound refers to an agent or compound that inhibits the infection or spread of CMV or the development of a CMV associated disease or disorder.

A pharmaceutical composition of the disclosure is formulated to be compatible with its intended route of administration. Examples of routes of administration include parenteral, e.g., intravenous, intradermal, subcutaneous, oral (e.g., inhalation), transdermal (topical), transmucosal, intravitreal, intracerebral, spinal and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS).

In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active agent/compound (e.g., a protein or anti-PDGF antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

The active agent/compound can be formulated for intravitreal administration. Such formulation can comprise slow release devices and materials (e.g., silicon or silicon oxide material). Such formulations are useful for the treatment of retinitis. In some embodiment, the active agent as described herein can be used in combination with other retinitis therapies (e.g., Vitravene® (fomivirsen)—an antisense drug to treat cytomegalovirus (CMV) retinitis in people with AIDS; developed by Isis and marketed by Novartis).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Slow release materials can also be obtained commercially from Alza Corporation and Nova Pharmaceuticals, Inc. Liposomal suspensions (including liposomes targeted to infected cells with monoclonal antibodies to surface (cell or viral) antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the $LD_{50}$ (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

The pharmaceutical compositions can be included in a container, pack, or dispenser together with instructions for administration.

The effectiveness, infectivity or treatment of a subject can be measured by commonly used techniques. For example, standard techniques used for determining CMV infection include those identified below. Accordingly, the usefulness and efficacy of an agent used for the treatment of or prevention of CMV infection can be measured. Conventional viral cultures of tissue biopsy or body fluid (e.g., buffy coat (WBCs), plasma, urine, respiratory secretions, or stool) can be used to measure infectivity. The specimen is incubated with fibroblasts at 36° C. for 1-3 weeks, and the fibroblasts are then examined under the microscope for cytopathic changes. The identification of cytomegalic inclusion bodies is used for the diagnosis of CMV disease or disorder. In another aspect, the shell vial culture technique in which the specimen is placed onto the fibroblast monolayer and centrifuged to help the virus penetrate the fibroblast, increases the viral yield 4-fold. The monolayer is stained 24-48 hrs later using monoclonal antibodies against a CMV protein produced during the immediate early phase of viral replication. In yet another aspect, the PP-65 antigenemia test is used wherein specific monoclonal antibodies are used to detect, in PMN leukocytes, a CMV matrix phosphoprotein known as pp-65. In a further aspect, CMV DNA is PCR amplified and detected. The PCR method is used either qualitatively (diagnostic PCR) or quantitatively to measure the viral load, which is proportional to the level of CMV DNA. CMV Serology Anti-CMV antibody (IgG and IgM) titers are routinely measured in both donor and recipient, primarily for the purpose of assessing the patient's risk for future development of CMV disease or disorder.

Also provided are methods for identifying modulators, i.e., candidate or test compounds or agents (e.g., peptides, peptidomimetics, small molecules, inhibitory nucleic acids, antibodies or other drugs) which bind to modulate the interaction of CMV with a PDGF receptor, or have a stimulatory or inhibitory effect on, for example, the kinase activity associated with a PDGF receptor.

Accordingly, assays for screening candidate or test compounds which modulate CMV-PDGF receptor interactions. Also provided are assays for screening candidate or test compounds which bind to or modulate the activity of the PDGF receptor, e.g., modulate the ability of the receptor to interact with its cognate ligand associated with the CMV viral coat. The test compounds can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach comprises peptide libraries, while the other four approaches are applicable to peptide, non-peptide oligomer or small molecule libraries of compounds (Lam, K. S. (1997) Anticancer Drug Des. 12:145).

Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994) J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and in Gallop et al. (1994) J. Med. Chem. 37:1233.

Libraries of compounds can be presented in solution (e.g., Houghten (1992) Biotechniques 13:412-421), or on beads (Lam (1991) Nature 354:82-84), chips (Fodor (1993) Nature 364:555-556), bacteria (Ladner U.S. Pat. No. 5,223,409), spores (Ladner USP '409), plasmids (Cull et al. (1992) Proc Natl Acad Sci USA 89:1865-1869) or on phage (Scott and Smith (1990) Science 249:386-390); (Devlin (1990) Science 249:404-406); (Cwirla et al. (1990) Proc. Natl. Acad. Sci. 87:6378-6382); (Felici (1991) J. Mol. Biol. 222:301-310); (Ladner supra.).

In another embodiment, an assay is a cell-based assay comprising contacting a cell expressing a PDGF receptor with a test compound and determining the ability of the test compound to modulate (e.g. stimulate or inhibit) the binding of the receptor to CMV, or a molecule associated with the viral coat of CMV.

Determining the ability of a target molecule, such as a PDGF receptor, to bind to or interact with CMV, or a molecule associated with the viral coat of CMV, can be accomplished by determining the activity of the target molecule. For example, the activity of the target molecule can be determined by detecting induction of a cellular second messenger of the target (e.g., a phosphorylation target for the PDGF receptor kinase), detecting catalytic/enzymatic activity of the target an appropriate substrate, detecting the induction of a reporter gene (comprising a target-responsive regulatory element operatively linked to a nucleic acid encoding a detectable marker, e.g., chloramphenicol acetyl transferase), or detecting a target-regulated cellular response.

In yet another embodiment, an assay provided herein can be a cell-free assay in which a PDGF receptor or biologically active portion thereof is contacted with a test compound and the ability of the test compound to bind to the PDGF receptor or biologically active portion thereof is determined. Binding of the test compound to the PDGF receptor can be determined either directly or indirectly.

In another embodiment, the assay is a cell-free assay in which a PDGF receptor or biologically active portion thereof is contacted with a test compound and the ability of the test compound to modulate (e.g., stimulate or inhibit) the activity of the PDGF receptor or biologically active portion thereof is determined. Determining the ability of the test compound to modulate the activity of a PDGF receptor can be accomplished, for example, by determining the ability of a PDGF receptor to bind to a target molecule, such as CMV or a molecule associated with the viral coat of CMV by one of the methods described herein for determining direct binding. Determining the ability of the PDGF receptor to bind to a target molecule can also be accomplished using a technology such as real-time Biomolecular Interaction Analysis (BIA). Sjolander, S, and Urbaniczky, C. (1991) Anal. Chem. 63:2338-2345 and Szabo et al. (1995) Curr. Opin. Struct. Biol. 5:699-705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

A cell-free assay provided herein can involve contacting a PDGF receptor or biologically active portion thereof with a known compound, such as CMV or a molecule associated with the viral coat of CMV, which binds the PDGF receptor to form an assay mixture, contacting the assay mixture with a test compound, and determining the ability of the test compound to interact with the PDGF receptor. This assay can determine the ability of the test compound to interact with the PDGF receptor and provide information related to the affinity of the receptor for CMV.

The cell-free assays described herein are amenable to use of both soluble and/or membrane-bound forms of proteins (e.g., PDGF receptor or biologically active portions thereof, or receptors to which binds). In the case of cell-free assays in which a membrane-bound form a protein is used it can be desirable to utilize a solubilizing agent such that the membrane-bound form of the PDGF receptor is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

Either a PDGF receptor or its target molecule (e.g., CMV or a molecule associated with the viral coat of CMV) can be immobilized to a solid support to facilitate separation of complexed from uncomplexed forms of one or both of the entities, as well as to accommodate automation of the assay. Binding of a test compound to a PDGF receptor, or interaction of a PDGF receptor with a target molecule in the presence and absence of a candidate compound, can be accomplished in any vessel suitable for containing the reactants. Examples of such vessels include microtitre plates, test tubes, and microcentrifuge tubes. In one embodiment, a fusion protein can be provided which adds a domain that allows one or both of the proteins to be bound to a matrix. For example, glutathione-S-transferase/fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of binding or activity determined using standard techniques.

Other techniques for immobilizing proteins on matrices can also be used in the screening assays provided herein. For example, either a PDGF receptor or a target molecule can be immobilized utilizing conjugation of biotin and streptavidin. Biotinylated protein or target molecules can be prepared from biotin-NHS(N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with PDGF receptor or target molecules but which do not interfere with binding of the PDGF receptor to its target molecule can be derivatized to the wells of the plate, and unbound target or PDGF receptor trapped in the wells by antibody conjugation. Methods for detecting such complexes, in addition to those described above for the GST-immobilized complexes, include immunodetection of complexes using antibodies reactive with the protein or target molecule, as well as enzyme-linked assays which rely on detecting an enzymatic activity associated with the PDGF receptor or target molecule.

Also provided herein are novel agents identified by the above-described screening assays. Accordingly, it is within the scope of this application to further use an agent identified as described herein in an appropriate animal model. For example, an agent identified as described herein (e.g., a modulating agent) can be used in an animal model to determine the efficacy, toxicity, or side effects of treatment with such an agent. Alternatively, an agent identified as described herein can be used in an animal model to determine the mechanism of action of such an agent. Furthermore, this application pertains to uses of novel agents identified by the above-described screening assays for treatments as described herein.

The following examples are offered to more fully illustrate the disclosure, but are not to be construed as limiting the scope thereof.

EXAMPLES

Cells and viruses. PDGFRα knock out parental 325S mouse fibroblasts were a obtained from Michelle Tallquist (Southwestern University, Andrews et al., Invest Ophthalmol V is Sci 40, 2683-2689 (1999)). Although HCMV is a human-specific virus and cannot be propagated in murine cells, HCMV internalization and HCMV immediateearly viral gene expression occur in murine cells. cDNA for human PDGFRα was obtained from Dr. Carl Heldin, Upsalla University, Sweden. HCMV strains AD169 and Towne (ATCC) were propagated in human embryonic lung fibroblasts (HEL cells) for less than five passages. HEL cells were infected at a MOI of 1 (in serum free media) and cell supernatant was collected over a period of 5-7 days following infection, when the cytopathic effect was ~100%. Virus containing media was first centrifuged (1500 g) to remove cell debris and further concentrated using a sucrose gradient centrifugation (80,000 g, 4° C.). Virus stock aliquots were kept at −80° C. Mock controls were generated in parallel by conditioning and processing uninfected cultures identically. Virus titers were determined by IE1 immunohistochemical staining. TR HCMV clinical isolate and GFP-CMV were obtained from Dr. W. Britt.

siRNA Experiments. HEL cells were transfected with 100 nM of either the "smart Pool" siRNA to hPDGFRα, human $p110^{PI3-K}$, or non-targeting siRNA pool (Dharmacon) using standard Lipofectamine 2000 reagent protocol (Invitrogen). 72 h following transfection, siRNA transfected cells were HCMV or mock infected. PDGFRα or $p110^{PI3-K}$ expression levels were measured using standard western blot and immunofluorescence analyses (antibodies from Cell Signaling).

Human embryonic lung fibroblasts HEL, U87 glioblastoma and HUVECs were obtained from ATCC and maintained in DMEM plus10% FCS, except for HUVECs which were grown in endothelial cell media (Cascade Biologicals), plus growth factors. Intestinal fibroblasts of mice homozygous for targeted deletion of a functional EGFR gene ($EGFR^{-/-}$) had been extensively characterized (Threadgill et al., 1995). Immortalized human astrocytes have previously been described (Sonoda et al., 2001). U251 glioblastoma and RK3E epithelial cell lines (Ruppert et al., 1991). MDA-MB468 human breast carcinoma (Kraus et al., 1987), NIH3T3 (Jainchill et al., 1969) and recombinant derivatives expressing human ErbB receptors including LTR-EGFR, LTR-ErbB2, LTR-ErbB3, LTR-ErbB4 and LTR-ErbB3+

ErbB2 have previously been characterized (Alimandi et al., 1995, Baulida et al., 1996, Fedi et al., 1994, Kraus et al., 1993).

Mouse PDGFRα knock out cells were transfected with human PDGFRα cDNA using Lipofectamine 2000 (Invitrogen) according to manufacturer's instructions. Towne-GFP (from Dr. W. Britt, UAB) is a recombinant HCMV strain that expresses GFP under the early promoter UL127, as described in Huang et al. J Virol 12, 1473-1481 (1973). Optimization of siRNA cell delivery was performed by co-transfecting with the targeting siRNA pools (e.g., PDGFRα siRNA) fluorescently labeled oligonucleotides (siGLO-RISC free, Dharmacon) that localize to the nucleus and permit assessment of uptake into cells. Targeting siRNA oligonucleotides and siGLO were mixed 1:1 (50 nM each) with different amounts of Lipofectamine 2000. 24 h later cells were fixed, counterstained with DAPI and counted. Average number of green fluorescent cells (a measure of transfection efficiency) was between 72-84% (from a total of 100% DAPI positive nuclei).

```
siRNA Sequences (listed 5'-3'):
PI3-K p110α
                              (SEQ ID NO: 5)
GCGAAAUUCUCACACUAUU, (SEQ ID NO: 6)
GUGGUAAAGUUCCCAGAUA, (SEQ ID NO: 7)
GCUUAGAGUUGGAGUUUGA, (SEQ ID NO: 8)
GACCCUAGCCUUAGAUAAA;

Human PDGFRα:
                              (SEQ ID NO: 1)
CGAGACUCCUGUAACCUUAUU, (SEQ ID NO: 2)
GAGCUUCACCUAUCAAGUUUU, (SEQ ID NO: 3)
GACAGUGGCCAUUAUACUAUU, (SEQ ID NO: 4)
GAAUAGGGAUAGCUUCCUGUU;

Non-targeting sequences:
                              (SEQ ID NO: 9)
UGGUUUACUAGUCGACUAA, (SEQ ID NO: 10)
UGGUUUACAUGUUUUCUGA, (SEQ ID NO: 11)
UGGUUUACAUGUUGUGUGA,
and (SEQ ID NO: 12)
UGGUUUACAUGUUUUCCUA.
```

Western Blot, Immunoprecipitation, and Immunofluorescence analyses. For stimulation experiments, cells were serum-starved for 24 h, followed by stimulation with HCMV (MOI of 0.5), PDGF-AA (5-10 ng/ml, from R&D Systems), or mock, for 10 minutes. In some cases, cells were pre-treated with IMC-3G3 (ImClone Inc.) at 10 g/ml (2 or 12 h) or Gleevec® (100 nM, 1 h) prior to HCMV exposure. Cell lysates were analyzed by SDS-PAGE. Antibodies used were as follows: polyclonal anti-PDGFRα (1/500), phosphor-Tyrosine clone 4G10 (1/1000), and monoclonal anti-p85 PI3-K (1/1000), (Upstate Biotechnology), anti HCMV IE1 MAB810 (Chemicon; 1/1000), anti HCMV pp65 (Novocastra, 1/1000), anti-phosphor-PDGFRα (1/500, pTyr 754), anti-phosphor-Akt (Ser 473, 1/1000) and total Akt (1/1000; all from Cell Signaling). Anti-actin polyclonal control antibody was used (1/500, Sigma). Immunoprecipitations were performed using protein G (Pierce) according to manufacturer's instructions. For immunofluorescence, monoclonal HCMV pp65 and phosphor-PDGFRα (p-Tyr 754, Santa Cruz Biotechnology) were used, overnight at 4° C., followed by 1 hour incubation with secondary antibodies conjugated to Alexa-488, or Alexa 568 (1/5,000, Molecular Probes). Nuclei were counterstained with DAPI. Co-immunoprecipitation experiments were performed using full length soluble purified recombinant gB (gB 680, from Don Diamond, City of Hope, Calif.) and detergent soluble extract of HEL cells generated in lysis buffer (1% NP-40, 75 mM NaCl and 50 mM Tris-HCl). 500 μg of protein from total cell extract was incubated with 25 μg of gB 680 in lysis buffer in the presence of an anti-gB (Virusys, Inc) or anti-PDGFRα (R&D) antibody overnight at 4° C. Immune complexes were recovered with protein A-Sepharose beads (2 hr incubation), denatured and separated on SDS-PAGE for western blot with anti-gB (Virusys, Inc) or anti-PDGFRα (Cell Signaling Technology) antibodies.

Viral Attachment and Internalization Assays. Mouse fibroblasts and HEL cells (72 hours following siRNA transfections) were incubated with HCMV (MOI of 0.5) or mock treated for 1 hour at 4° C., after which cells were returned to 37° C. for 15, 30, or 60 min. Cells were fixed using methanol (20 min) and processed for pp65 immunofluorescence. Four low power fields were counted for each condition and pp65 positive were recorded for each 100 cells. Internalization assays were repeated twice.

HCMV Glycoprotein B (peptide) Attachment Assays. gB peptide binding experiments were performed similar to viral attachments assays. After 1 h incubation with the gB peptide (100 nM, 4° C.), cells were returned to 37° C. for 60 min, washed, fixed, and processed for double immunofluorescence for gB (1 μg/ml, monoclonal antibody, Virusys Corp) and PDGFRα (2 μg/ml, Upstate). The gB peptide (Ray Biotech) contains amino acids 27-84 from the AD169 strain and 27-81 from the Towne strain.

Human Phospho-PDGFRα ELISA. ELISA for human Phospho-PDGFRα was performed with a kit (R&D, cat. #DYC2114-2). HEL cells were grown in 24 well plates (40,000 cells/ml) and serum starved 48 h prior to short term (10 min) stimulation with various agents, as described in FIGS. 2b and 4d. Lysis of cells was done per kit instructions. The capture antibody was a mouse anti-human PDGFRα; anti-phosphotyrosine-HRP antibody was used for detection. Recombinant human phosphorylated PDGFRα was used as a positive control. Reaction products were read using a microplate reader set at 450 nm. All samples were run in triplicates and each experiment was repeated at least twice. For receptor blocking experiments, cells were pretreated with IMC-3G3 (10 μg/ml, 12 h) or Gleevec® (100 nM, 1 h). To test the effects of gB neutralizing antibodies, HCMV (MOI of 1) was pre-incubated in serum free media with antibodies gB 7-17, MAB 758, or control isotype matched antibodies (5 μg/ml) for 1 h prior to cell stimulation. Additional antibodies tested included neutralizing antibody against HCMV gN (Isomura et al. J Virol 77, 3602-3614 (2003)) and gH (Britt et al., J Virol 79, 4066-4079 (2005)).

Measurements of Infectious Virus Production. HEL cells (where indicated were treated with siRNA) were infected with HCMV Towne or CMV-GFP for 1 h, washed and grown for 6 days at 37° C. A duplicate set of cultures was analyzed by immunofluorescence at 12 hours post infection (hpi) to assess percent of IE1 positive cells, as a measure of "primary infection". Six days post infection supernatant from these cells were centrifuged to exclude cell debris and used to infect naïve HEL cultures as described above. 12 hpi cells were stained for IE1 and IE1 positive cells were counted amongst a total of 100 cells/low magnification microscopic field, 4 fields/condition. These counts were used to determine the level of "secondary infection"—i.e., infectious virus production from the primary infected cells. Where indicated, CMV-GFP infected cells were monitored daily under fluorescence microscope. Each condition was assayed in triplicate.

Plaque Formation Assays. Plaque formation was assayed. Confluent HEL cells in 6 well cluster plates were incubated with Towne-GFP (MOI of 1, 1 hr) in 0.5 ml growth media. Cells were washed and returned to 37° C. (in complete growth media). 24 h later supernatant was harvested and used to infect naïve HEL cultures which were monitored for plaque formation for 6-14 days. Plaque formation was photographed daily using an inverted fluorescent microscope. At day 14, plaques in ten low magnification fields/condition were counted (each experimental condition was tested in 6 independent wells).

Statistical analyses. Two-tailed paired Student T test was used to compare data sets and obtain p-values for all comparisons; p values are indicated on figure panels.

Figure 5:
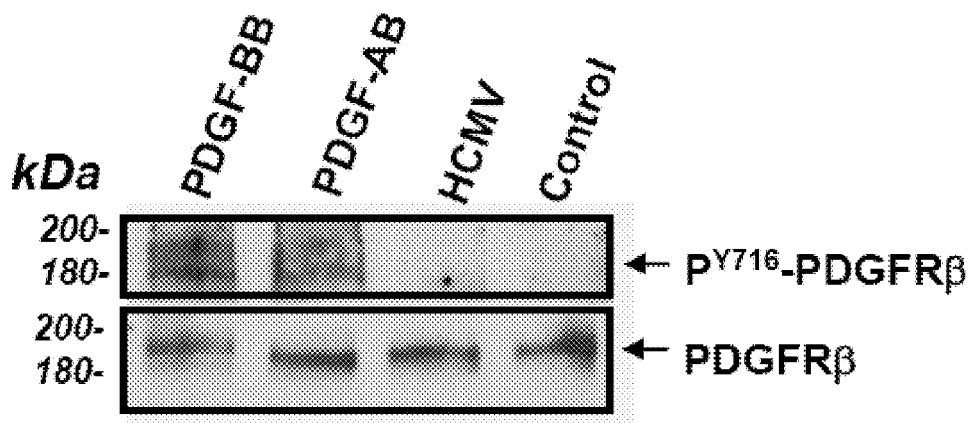
FIG. 5 shows that HCMV does not induce tyrosine phosphorylation of Platelet Derived Growth Factor Beta Receptor (PDGFRβ). Serum starved HEL cells were stimulated for 10 minutes with recombinant human PDGF-BB (10 ng/ml; from R&D systems), PDGF-AB (10 ng/ml, from R&D Systems), HCMV (MOI of 1) or mock (Control). Subsequently, cells were washed with cold PBS, and collected in lysis buffer supplemented with protease and phosphatase inhibitors. The soluble fraction of cell lysates were subjected to SDS-PAGE and western blot analyses using the phosphor-specific antibody Tyr 716-PDGFRβ (2 μq/ml, Upstate), upper panel. The same membrane was stripped and re-probed for total PDGFRβ (2 μg/ml, Upstate), shown in the lower panel. Only PDGF-BB and PDGF-AB induce phosphorylation of Tyr 716 on PDGFRβ.
Figure 6:
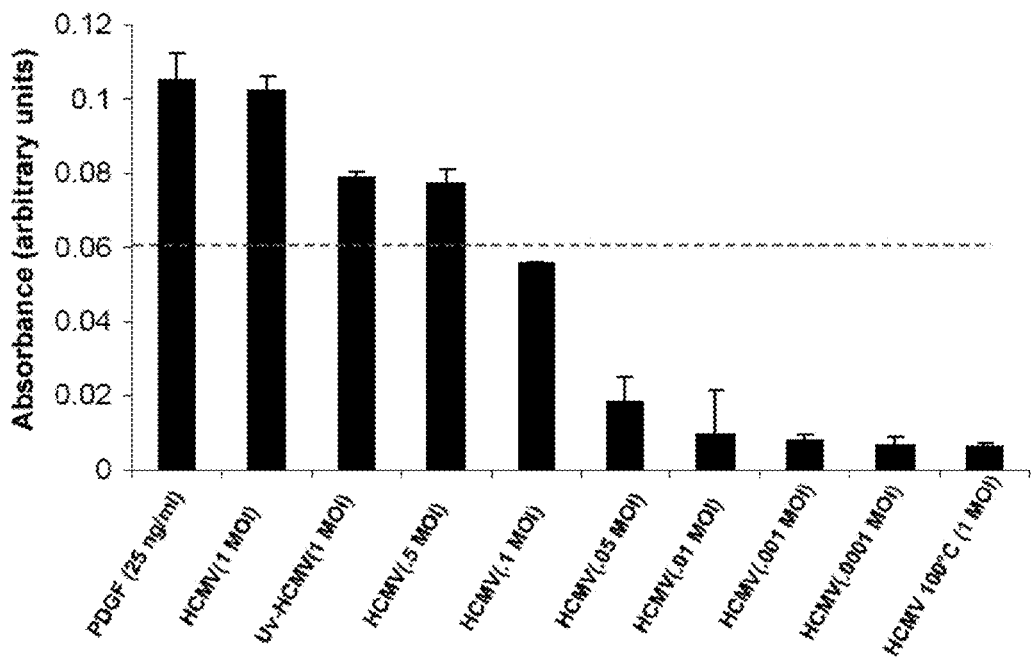
FIG. 6 shows UV-inactivated, but not heat-inactivated HCMV induces PDGFRα tyrosine phosphorylation. Serum starved HEL cells were stimulated for 10 minutes as indicated, and lysed. The lysates were used in a "sandwich" ELISA for human phosphor-PDGFRα according to the manufacturer's instructions (DYC114-2, R&D). Both HCMV (MOI>0.1) and UV-inactivated (20 min) HCMV (MOI of 1) induced PDGFRα tyrosine phosphorylation to levels comparable with that induced by the genuine ligand, PDGF-AA. Virus inactivated by boiling (5 min) did not induce receptor phosphorylation. A series of dilutions from the virus stock were tested, between an MOI of 1 to MOI of $10^{-5}$. Note that PDGFRα phosphorylation levels induced by HCMV used at MOI<0.1 are below the optimum detection limit for the assay, represented by the red dotted line which corresponds to the absorbance values obtained using 4000 pg/ml of recombinant phosphor-PDGFRα. Average±SD (n=6) absorbance values are shown.

To identify this putative RTK, a human phospho-specific RTK antibody array was used to screen human embryonic lung fibroblasts (HEL) either mock or HCMV (Towne strain) infected for 10 minutes. Only platelet derived growth factor-α receptor (PDGFRα) was highly tyrosine phosphorylated upon HCMV infection (FIG. 1a). Western blot analyses of these same protein lysates using a different phospho-specific antibody for PDGFRα corroborated this observation (FIG. 1b). Independent quantitative ELISA assays confirmed PDGFRα phosphorylation by Towne, AD169, and TR[21] strains (FIG. 1c). HCMV did not induce tyrosine phosphorylation of the related RTK, PDGFRβ (FIG. 5). UV inactivated HCMV induced PDGFRα phosphorylation, while virus inactivated by heat did not (FIG. 6).

To determine whether the HCMV-induced PDGFRα phosphorylation was cell type specific, U87 glioma (neuro-epithelial origin), HEL (fibroblast), and human umbilical vein endothelial cells (HUVEC, mesenchymal origin) were used. In all three cell types, infection with HCMV Towne induced PDGFRα phosphorylation, similar to the genuine ligand (FIG. 1d).

Figure 2:
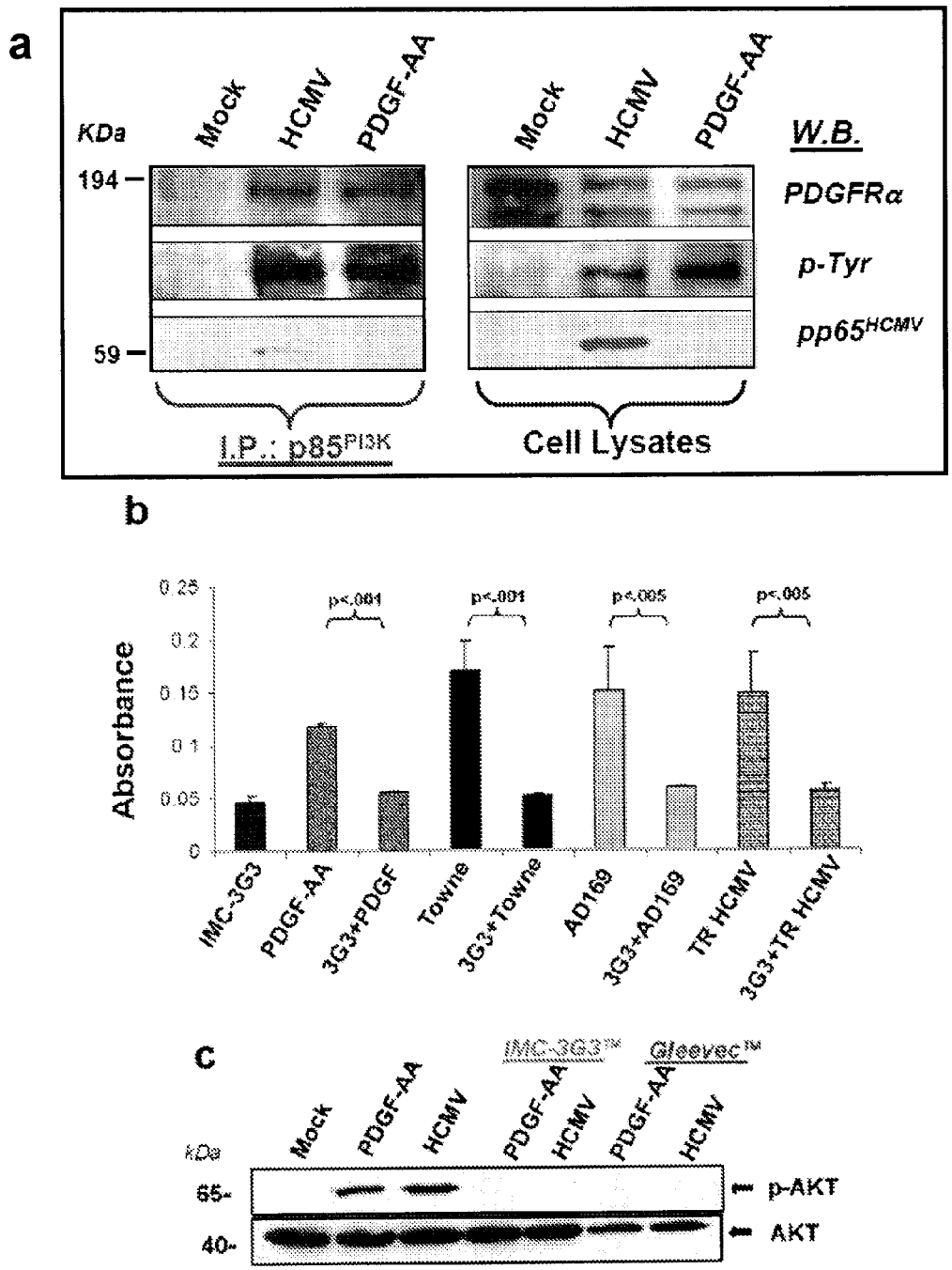
FIG. 2A-C shows that HCMV activates the PI3-K/Akt pathway in a PDGFRα-dependent manner. (A) HEL cells stimulated with HCMV or PDGF-AA were subjected to immunoprecipitation and western blot analyses with indicated antibodies. (B) Phospho-PDGFRα ELISA of cells+/− pretreatment with IMC-3G3 (10 μg/ml, 2 h) followed by HCMV (MOI=1) or PDGF (10 ng/ml) for 10 min. Mean values (n=6)±S.D are shown. (C) Western blot of HEL mock, HCMV, or PDGF-AA stimulated (10 min), +/−IMC-3G3 (2 μg/ml) or Gleevec® (Imatinib) (100 nM). The same membrane was used for p-Akt$^{Ser\ 473}$ and Akt.

Based on these data, it was hypothesized that PDGFRα was the ~180 kDa protein identified associated with the p85 regulatory subunit of PI3-K, upon HCMV attachment. To confirm this, co-immunoprecipitation experiments in HCMV or mock infected cells were performed. Immunoblotting of $p85^{PI3-K}$ immunoprecipitated proteins and whole cell lysates with antibodies specific for PDGFRα and phosphotyrosine indicated that PDGFRα was tyrosine phosphorylated and associated with $p85^{PI3-K}$ upon HCMV short term stimulation (FIG. 2a). Specificity of PDGFRα phosphorylation by the Towne, AD169, and TR strains was examined in the presence or absence of IMC-3G3, a humanized PDGFRα blocking antibody (ImClone Inc.). Pre-treatment with IMC-3G3 significantly inhibited PDGFRα phosphorylation induced by all HCMV strains tested (FIG. 2b). To investigate HCMV-induced activation of the downstream PI3-K/Akt signaling, both the IMC-3G3 antibody, and a PDGFRα kinase inhibitor, imatinib mesylate (Gleevec®) were used to block either PDGFRα binding or its activation. Akt phosphorylation induced by either HCMV or PDGF-AA was abolished by IMC-3G3 and Gleevec (FIG. 2c). An isotype matched negative control antibody did not inhibit HCMV- or PDGF-induced PDGFRα or Akt phosphorylation. Thus, blocking PDGFRα or inhibiting its activity prevents HCMV-mediated activation of the PI3-K/Akt signaling pathway, an important pathway in the HCMV viral life cycle.

Figure 3:
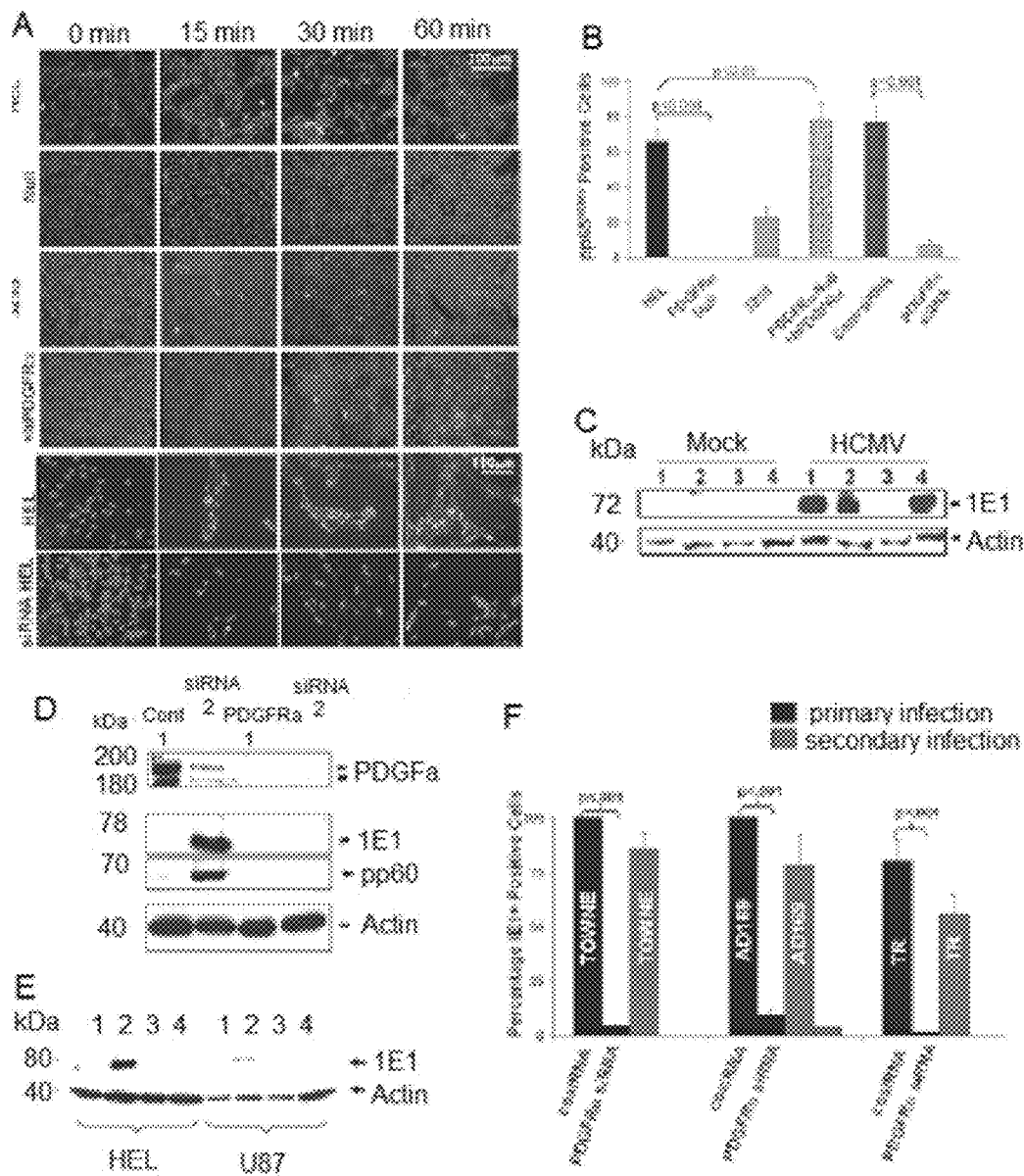
FIG. 3A-F shows human PDGFRα is required for HCMV entry, IE1 expression, and infectious virus production. (A) pp65 immunofluorescence after HCMV treatment (1 h, 4° C.) followed by shifting to 37° C. for indicated times. Rows represent (top to bottom): HEL, PDGFRα null fibroblasts, parental fibroblasts, null fibroblasts overexpressing hPDGFRα, HEL transfected with control, or PDGFRα siRNA. Nuclei were stained with DAPI. (B) Average±S.D. pp65 positive/100 cells counted in triplicate from (A). (C) Mock or HCMV infected cells were analyzed by western blotting with the indicated antibodies. Lanes 1-4 indicate HEL, 325S, PDGFRα null and PDGFRα null over-expressing hPDGFRα, respectively. (D) HEL transfected with control or PDGFRα siRNA were mock (lanes 1) or HCMV-treated (lanes 2) and subjected to western blots with indicated antibodies. (E) Western blot of HEL and U87 lysates after infection with mock (lanes 1), HCMV (lanes 2), or HCMV pretreated with IMC-3G3 (10 μg/ml, 12 h, lanes 3) or Gleevec (100 nM, 1 h, lanes 4). (F) PDGFRα siRNA treated cells infected with indicated HCMV strains and immunostained for IE1 12 hpi (primary infection). 6 dpi, supernatants were used to infect naïve HEL cells, followed by IE1 immunostaining and quantification (secondary infection). Average (n=6) values±S.D. are shown.

To determine whether PDGFRα is critical for viral internalization and gene expression, a well-characterized viral entry assay was used to measure internalization of the pp65 viral tegument protein after HCMV-treated cells are shifted from 4° C. to 37° C.[24] Human and murine cells engineered to knockout, knockdown, or overexpress PDGFRα were used. As shown in FIG. 3a, 60 min after shifting to 37° C., HEL cells demonstrate evidence of viral internalization, indicated by immunostaining of nuclear pp65 in over 65% of cells per microscopic field (upper row). siRNA-mediated knockdown of PDGFRα (FIG. 3a, lower two panels), caused near complete blockade of viral internalization, compared to the non-targeting, control siRNA treated cells (p<0.001, FIG. 3b). Similarly, murine fibroblasts obtained from embryos of PDGFRα knockout mice (embryonic lethal), showed no pp65 positive nuclei (3a, upper second row) whereas in fibroblasts from parental strain (325S) over 25% of cells were pp65 positive (3a, upper third row). Re-introducing human PDGFRα into the knockout cells restored and augmented HCMV internalization in these cells (3a, fourth row from the top, 80% of cells are pp65 positive) even compared to positive control cells (FIG. 3b, p<0.01, student T test).

Figure 7:
FIG. 7 shows that IMC-3G3 and Gleevec prevent HCMV IE1 expression in HUVEC. HUVEC cells were pre-treated with IMC-3G3 (10 μg/ml, Imclone, 12 h), or Gleevec (100 nM, 1 h) prior to HCMV or mock infection. 12 hours post-infection, cell lysates were analyzed by western blot for the presence of IE1 gene product. Both the IMC-3G3 antibody and Gleevec completely inhibited IE1 expression in HCMV-treated HUVEC (upper panel). The same blot was stripped and re-probed for actin (lower panel). Lane designation is 1—Mock, 2—HCMV, 3—IMC-3G3+HCMV, 4—Gleevec+HCMV.

To determine whether genetic ablation of PDGFRα prevents cellular expression of essential HCMV gene products expression of IE1 (UL123) in murine cells, as well as IE1 and pp65 (UL83) in human cells following infection with HCMV was performed. Viral gene expression was undetectable in the PDGFRα knockout murine cells (FIG. 3c) and in the human HEL cells pre-treated with PDGFRα siRNA (FIG. 3d), compared to controls. Prolonged activation of human PDGFRα by HCMV resulted in down-regulation of receptor levels (FIG. 3d, upper panel, lane 2, in control siRNA treated cells). IE1 expression was also undetectable following infection of the PDGFRα null mouse fibroblasts with the AD169 strain, indicating that this effect is not strain specific. Pre-treatment with PDGFRα blocking agents IMC-3G3 antibody and Gleevec, completely inhibited HCMV IE1 gene expression in human HEL and U87 glioma cells (FIG. 3e) as well as in HUVEC (FIG. 7).

Figure 8:
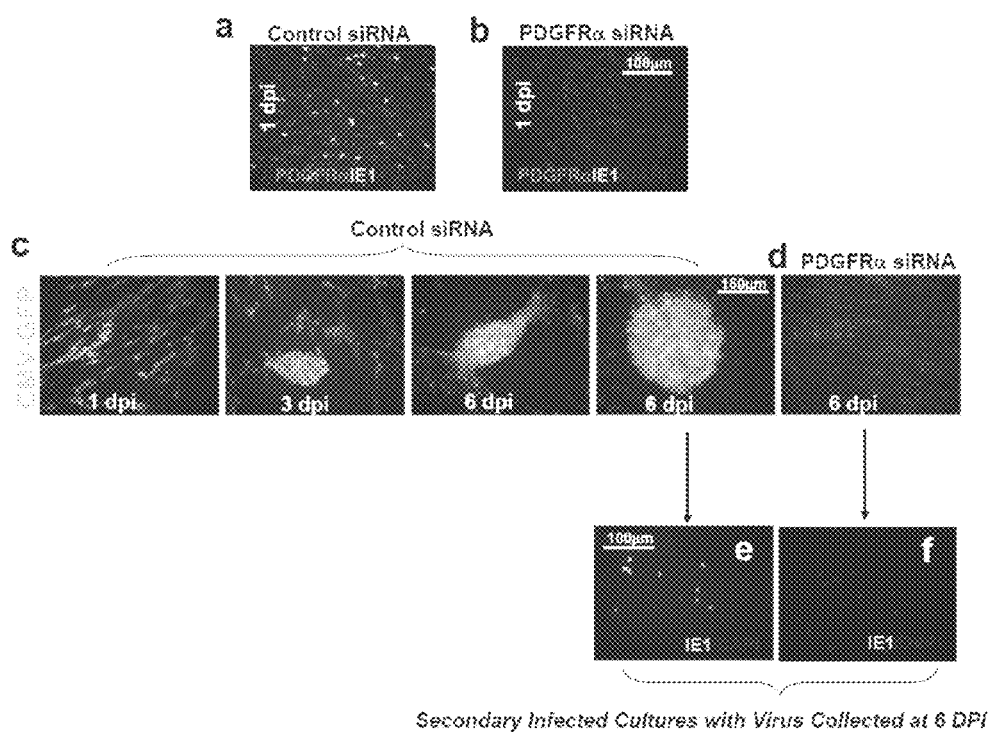
FIG. 8A-F shows that knockdown of PDGFRα at the time of infection inhibits production of infectious virus. HEL cells were transfected with PDGFRα siRNA (smart pool, Dharmacon) or non-targeting control siRNA (Dharmacon) for 48-60 hours when maximum protein knockdown is achieved (panels a and b. Also see FIG. 3d). Cells were then infected with Towne, AD169, TR, or CMV-GFP strains of HCMV for 1 hour, washed and returned to 37° C. in complete growth media. Supernatants obtained from these cultures were used in subsequent assays measuring production of infectious virus as described below. One set of cultures (panels a and b) were used 12 hours post-infection (12 hpi) to measure the expression level of PDGFRα and IE1 by immunofluorescence. PDGFRα knockdown significantly inhibited IE1 gene expression compared to control siRNA transfected cells (compare green fluorescent cell nuclei in panels a and b). PDGFRα immunodetection at 12 hpi shows significant decrease in receptor levels, as shown by red fluorescent cells in panels a and b. Cultures infected with supernatants from GFP-CMV treated cells were monitored daily under the fluorescence microscope. Over 40% of the control siRNA treated cells expressed CMV-GFP 1 day post infection (c, 1 dpi) and this number increased to 100% by day 6 (c, 6 dpi). Note the appearance of "plaques"-like groups of cells in control siRNA transfected cells (c, 3 and 6 dpi). In contrast, PDGFRα siRNA treated cells did not express CMV-GFP (d). To measure infectious virus production, supernatants from both control and PDGFRα siRNA treated cultures were harvested at 6 dpi and used to infect naïve HEL cells (secondary infection). PDGFRα siRNA treated cells did not produce any infectious virus, as demonstrated by the lack of IE1 positive cells in the secondary infected cultures (f), while cells infected with supernatant from control siRNA treated cultures were positive for IE1 (e). These experiments were repeated twice.
Figure 9:
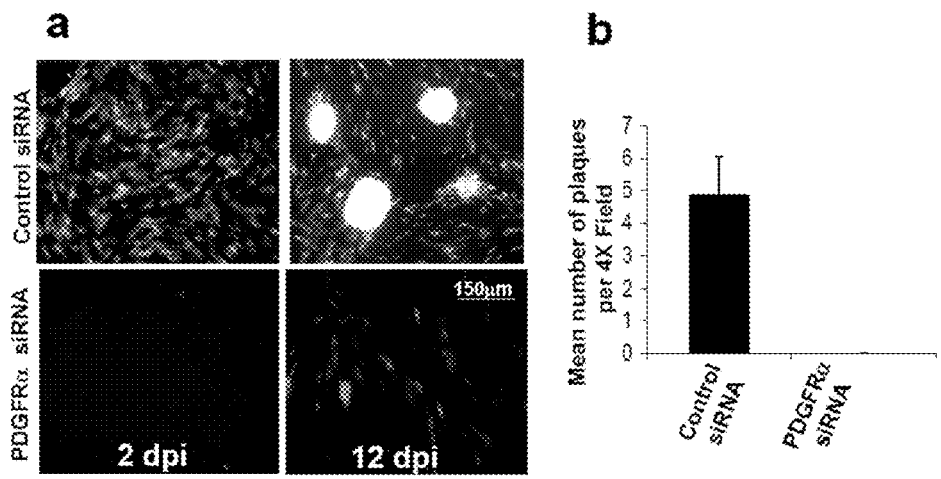
FIG. 9A-B shows that PDGFRα knock down at the time of infection inhibits plaque formation. a. HEL cells transfected with PDGFRα siRNA and control cultures were infected with CMV-GFP (MOI of 1), as described in FIG. 8. Unabsorbed viruses were washed and cells were returned to 37 C. 24 h later, supernatant was harvested and used to infect naïve HEL cultures (6 wells/condition) which were monitored daily for 14 days under the fluorescence microscope for plaque formation. Photomicrographs show representative examples of the CMV-GFP infected cells at 2 and 12 days post infection (2 dpi and 12 dpi, respectively). b. Average plaques counted in 4 separate low magnification fields for each well at 14 dpi. No plaques were formed in the PDGFRα siRNA treated cells. These results suggest that the absence of a functional PDGFRα at the time of infection prevented plaque formation. As receptor levels return to normal (12 dpi), few infected (green fluorescent) cells were detected in the PDGFRα siRNA treated cultures (a, lower right panel), without formation of plaques. Plaque formation assays were repeated twice. Average counts (n=12)±SD are shown.

Investigation of whether PDGFRα expression was required for production of infectious virus using siRNA knockdown of PDGFRα in HEL cells and a Towne-GFP[24] virus was performed for visualization of infected cells and plaque formation. 48-60 hours following siRNA transfection, HEL cells were exposed to HCMV for one hour and monitored daily under a fluorescent microscope. Duplicate cultures were used for IE1 staining at 12 hpi, while a third set of cultures was used to measure plaque formation (FIGS. 8 and 9). Six days post infection supernatants of these cells were used to infect naïve HEL cells and asses production of infectious virus (FIG. 3f and FIG. 8). Near complete inhibition of both viral gene expression and infectious virus production was observed in cells that do not express PDGFRα at the time of infection. Plaque formation in HEL cells was also completely blocked by PDGFRα knockdown (FIG. 9).

Figure 10:
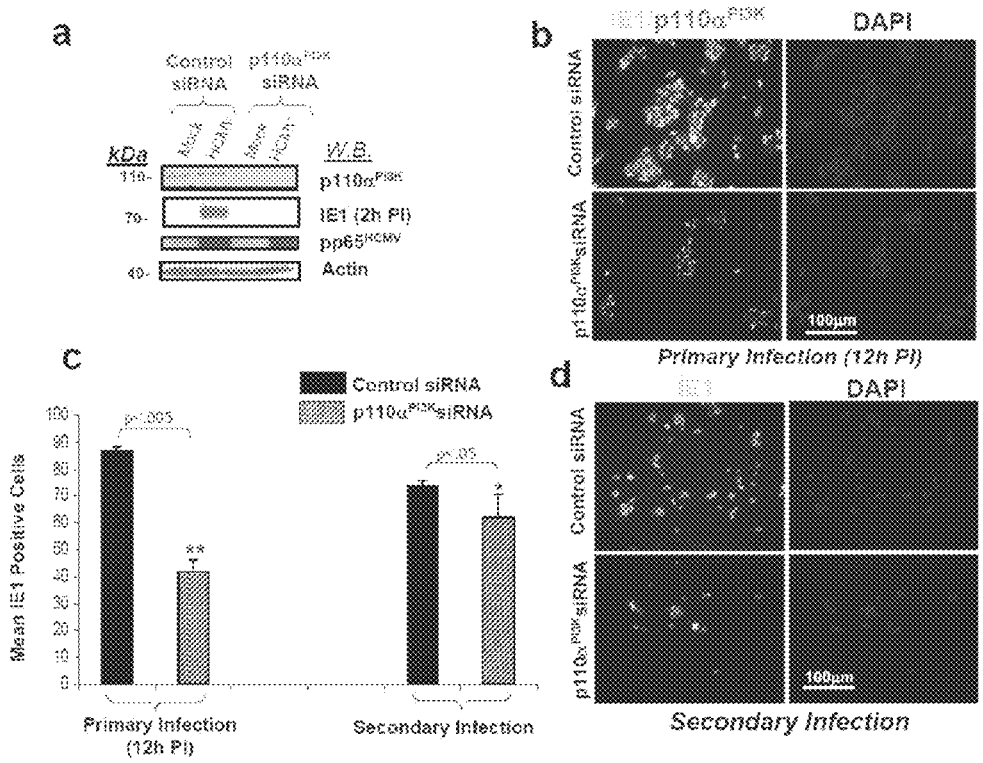
FIG. 10A-D shows that PI3K p110α knock down inhibits HCMV gene expression and infectious virus production. HEL cells were transfected with siRNA against the PI3K p110α catalytic subunit (a mixture of 4 RNAi oligos, "smart pool" from Dharmacon) or non-targeting, control siRNA (Dharmacon) for 48 h prior to infection with HCMV (MOI of 1) for 1 hour. Cells were washed and cultured for 2 h-6 days. a. Western blot analysis 2 h post-infection indicates that IE1 expression is inhibited by PI3K p110α knockdown. Western blot of PI3K p110α indicates efficient knockdown by siRNA relative to actin which remains unchanged. pp65$^{HCMV}$ expression was unchanged in PI3K p110α knockdown cells, indicating that viral entry is not inhibited. b. Double immunofluorescence analyses revealed a significant reduction in IE1 expression levels (green fluorescence, left panels) in the p110α knockdown cells. The mean number of IE1 positive cells is reduced by ~50% in the PI3 Kp110α knockdown cultures—panel c**, p<0.01. PI3K p110α knock down is also significant (b, left panels, red fluorescence). However, unlike cells that lack a functional PDGFRα, PI3K p110α knock down cells are capable of producing infectious virus as shown by IE1 staining of the secondary infected cultures (panel d). A 10% decrease in infectious virus production in the cells treated with p110α siRNA is insignificant*, bars represent SD, p<0.5, panel c. Experiments were repeated twice, all conditions were assayed in triplicate. Similar results were obtained with both Towne-infected cultures (illustrated in this figure) and CMV-GFP.

To determine the relative importance of PDGFRα versus downstream PI3-K activation for viral gene expression and infectious virus production, a series of experiments using $p110α^{PI3-K}$ siRNA and non-targeting siRNA treated cells was performed. Suppression of the PI3-K pathway by p110α knockdown resulted in a delay in viral gene expression, yet allowed viral entry, and infectious virus production albeit at lower levels than controls in agreement with previous studies using PI3-K inhibitors (FIG. 10). These data indicate that although PI3-K activation is important for the HCMV lifecycle, expression of a functional PDGFRα is essential.

Figure 4:
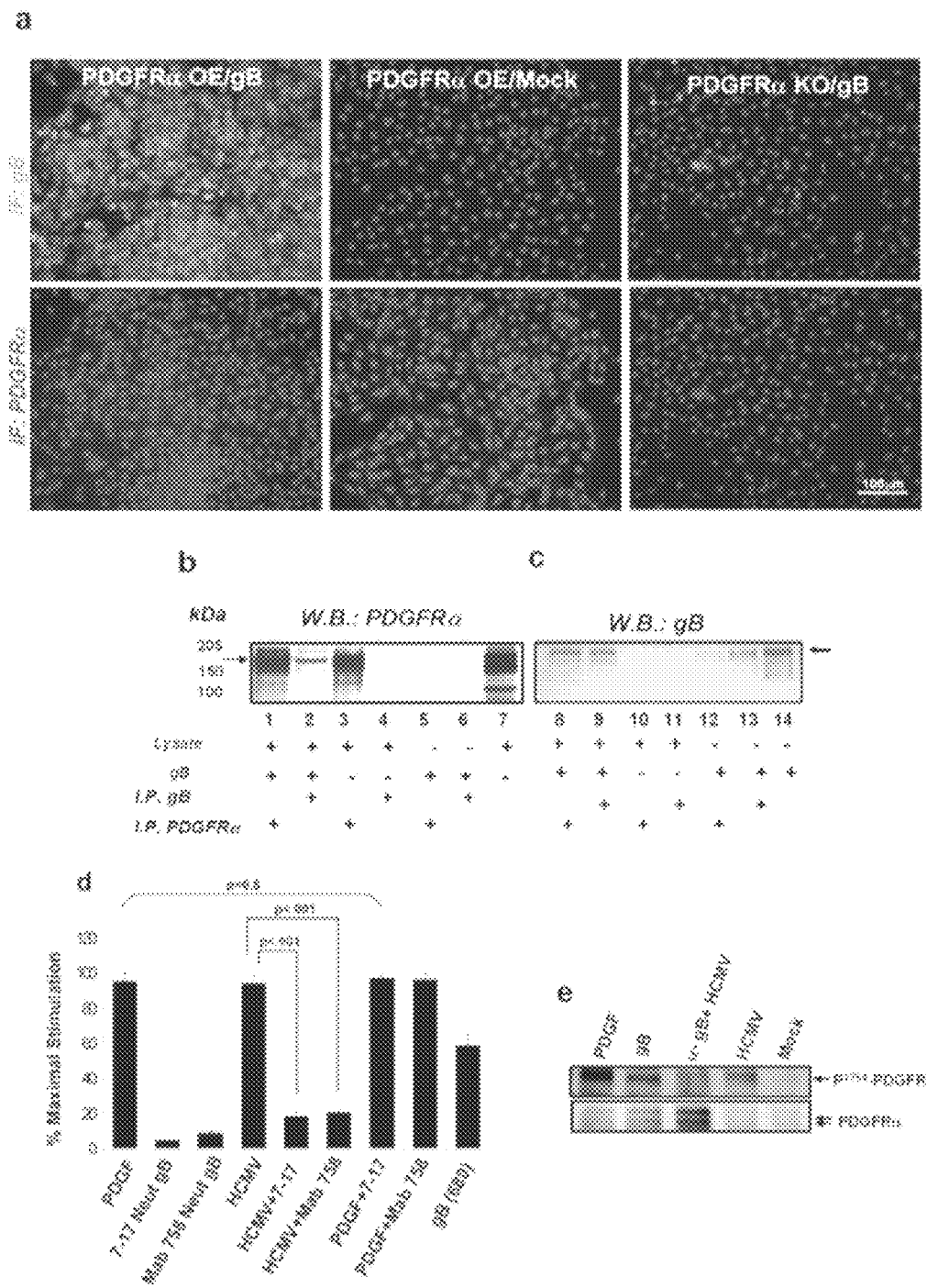
FIG. 4A-E shows HCMV Glycoprotein B binds and activates PDGFRα. (A) Immunofluorescence detection of gB (upper panels) and PDGFRα (lower panels) in PDGFRα KO cells and PDGFRα overexpressing (OE) cells, following incubation with the gB peptide or mock treatment. Reduced PDGFRα surface staining in gB-treated cells is likely due to receptor internalization. (B) and (C) Immunoprecipitation of PDGFRα and gB from HEL lysates and full-length soluble gB alone or pre-incubated together. Immunoprecipitates were subjected to western blot with the indicated antibodies. (D) ELISA of hPDGFRα phosphorylation after HCMV stimulation (MOI=1), PDGF (10 ng/ml) or recombinant soluble gB (30 μg/ml) in presence or absence of gB neutralizing antibodies 7-17 and Mab 758 (5 μg/ml); bars, ±S.D. (E) Portions of same lysates used in (D) were analyzed by western blot with indicated antibodies.
Figure 11:
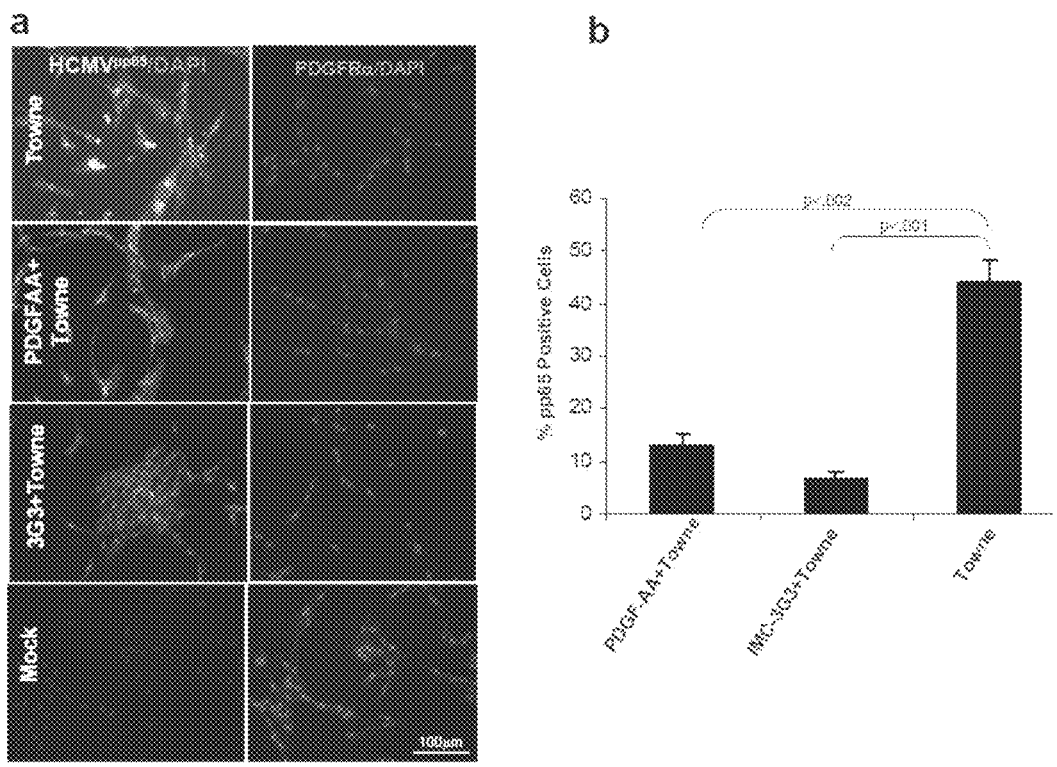
FIGS. 11A-B shows PDGF-AA competitively inhibits HCMV entry. (A) HEL cells were pretreated with PBS (20 min 4° C.), IMC-3G3 (2 h, 37° C., 10 μg/ml), or PDGF-AA (20 min, 4° C., 10 ng/ml) prior to infection with HCMV (MOI of 1, 4° C., 1 h). Cells were returned to 37° C. for 30 minutes, and processed for pp65$^{HCMV}$ and PDGFRα double immunofluorescence. PDGFRα expression levels (red fluorescence) appear most down-regulated in the PDGFAA+Towne treated cells, suggesting receptor internalization. (B) Quantification of pp65 positive cells indicates that pretreatment with PDGF-AA and IMC-3G3 inhibits HCMV entry by ~30% and ~45%, respectively. All conditions were assayed in triplicate cultures. One hundred cells in 4 low magnification fields were counted. Bars represent SD.
Figure 12:
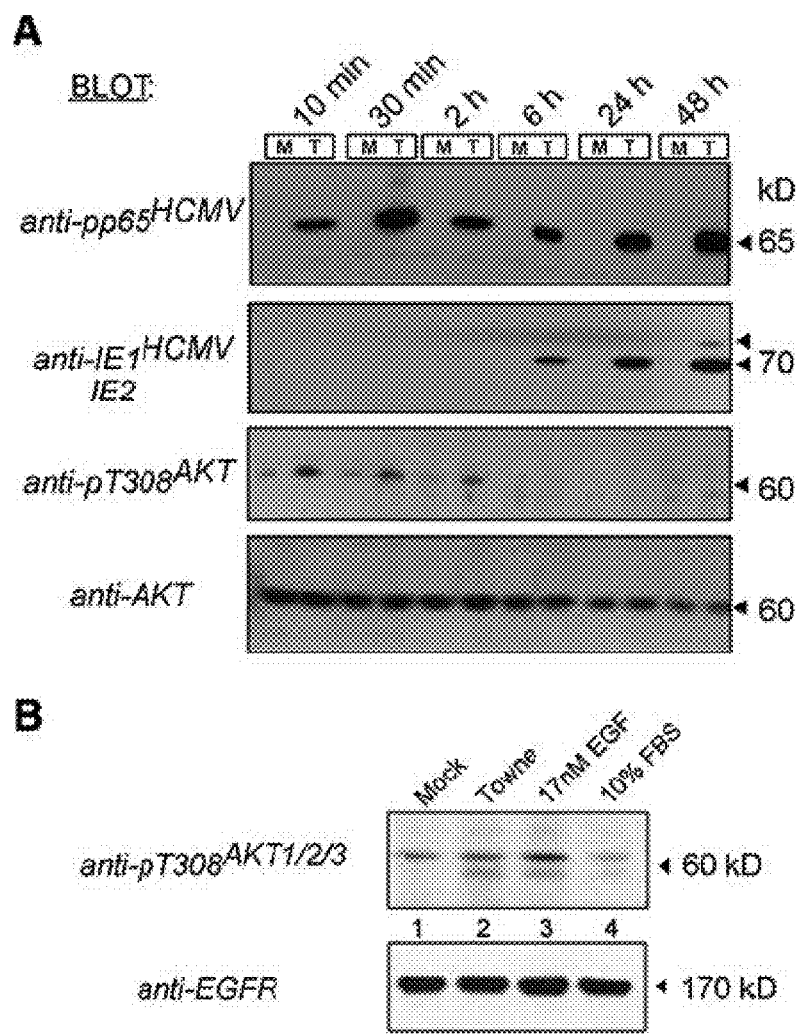
FIG. 12A-B shows rapid activation of PI 3-K effector AKT kinase by HCMV in human astro-glial cells and embryonic lung fibroblasts. (A) Time course of HCMV infection and AKT induction in NHAs; cells were serum-starved and mock treated (M) or infected with HCMV Towne strain (T). Immunoblot analysis shows the presence of HCMV pp65 protein 10 minutes following stimulation, while IE1/IE2 viral gene products become detectable 6 h following stimulation. pT308-AKT reaches maximum levels at 10 minutes following HCMV stimulation reminiscent of growth-factor-induced signaling. (B) Short-term (10 min) Towne triggering of HEL cells results in phosphorylation of AKT to a similar extent as the p-AKT induced by EGF.
Figure 13:
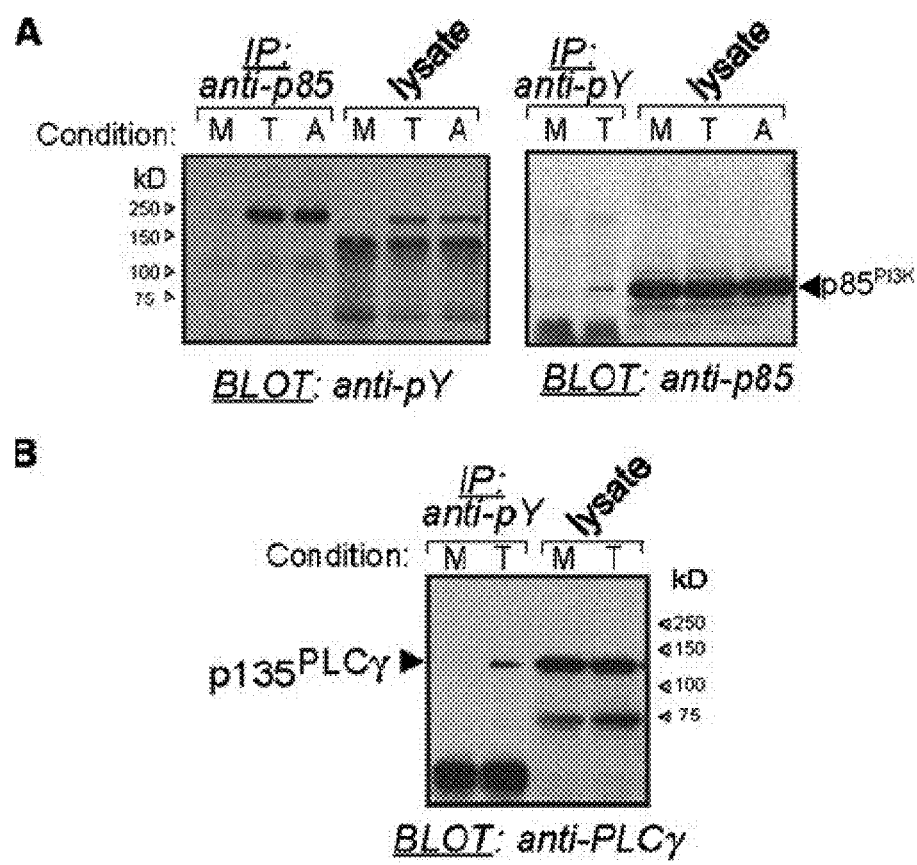
FIG. 13A-B shows recruitment of phospholipid substrate pathways PI-3K and PLCγ by HCMV-mediated activation of tyrosine kinase signaling. Serum-starved HEL cells were treated as indicated: M=mock, T=Towne, A=AD169. (A) Immunoprecipitates using either anti-p85 antibody (UBI 06-195; left) or anti-phosphotyrosine MAb pY99 (sc-7020AC; right) were blotted using anti-pY99 (sc-7020; left panel) or anti-p85 (right panel), respectively. Towne and AD169 treated samples display the presence of a ~180-200 kDa protein phosphorylated on Tyrosine, also present in the cell lysates (left panel). Several cellular p-Tyr proteins associated with p85 are detectable in the Towne-infected samples (right panel). (B) Four hundred μg fresh lysates were immunoprecipitated using anti-pY99 agarose conjugate and blotted using an anti-PLCγ MAb; association of PLCγ with cellular phosphotyrosine proteins is noticeable only in the Towne-infected samples.
Figure 14:
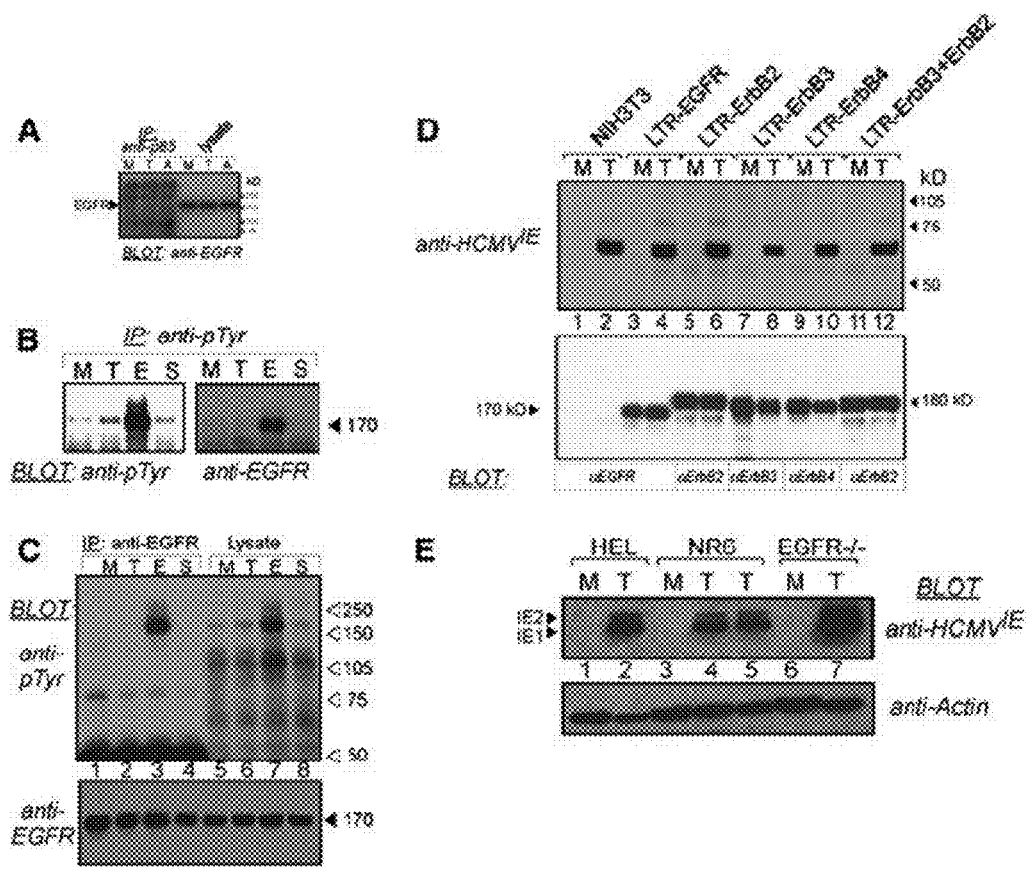
FIG. 14A-E demonstrates lack of direct EGFR activation in vivo by HCMV. (A) Re-blotting of anti-p85 co-immunoprecipitates and lysates (FIG. 2 panel A) using EGFR peptide antiserum demonstrates the lack of association between p85 and EGFR, following either Towne or AD169 stimulation. (B) Cells were stimulated using HCMV Towne (MOI~5; T), EGF (E) and serum (S); lysates (200 μg) were immunoprecipitated using anti-pY20 phosphotyrosine MAb and evenly divided for immunoblot analysis using anti-pY20 and EGFR peptide antiserum E7. Only stimulation using EGF results in p-Tyr of EGFR, while Towne treatment induced p-Tyr of a ~180-200 kDa protein, distinct from EGFR. (C) Immunoprecipitates of the EGFR extracellular domain were divided and subjected to immunoblot analysis using anti-pY20 (upper panel) and EGFR peptide antiserum E7 (lower panel). Again, only EGF stimulation (lane E) results in p-Tyr of EGFR, which is present at equivalent levels across all samples. (D) ErbB family members are not required for immediate early gene expression of HCMV. NIH3T3 fibroblasts over-expressing individual human ErbB receptors or an ErbB3-ErbB2 heterodimer (Alimandi et al., 1995, Baulida et al., 1996, Fedi et al., 1994, Kraus et al., 1993) were mock treated (M) or infected (T) for 2 h. Protein lysates were subjected to immunoblotting using HCMV IE1 (Mab810) or ErbB receptor antibodies E7, M6, MK4 and E4 to confirm recombinant Erb1-4 overexpression in the respective transfectants (Alimandi et al., 1995, Baulida et al., 1996, Fedi et al., 1994, Kraus et al., 1993). Towne treatment resulted in robust IE1 expression on all the cell lines tested, including the NIH3T3 un-transfected, parental cells, demonstrating that human Erb1-4 receptors are not rate-limiting for HCMV infection. (E) HEL cells, NR6 cells representing an EGFR-negative derivative of NIH3T3 (Di Fiore et al., 1987, Pruss & Herschman, 1977), and fibroblasts from EGFR −/− mice (Threadgill et al., 1995) were mock treated (M) or infected with HCMV Towne (T) for 6 h (lane 4) or 24 h (lane 2, 5, 7). IE1 expression as determined by Western blot analysis using MAb810, shows that even in the absence of the EGFR gene, cells maintain their susceptibility to HCMV infection.
Figure 15:
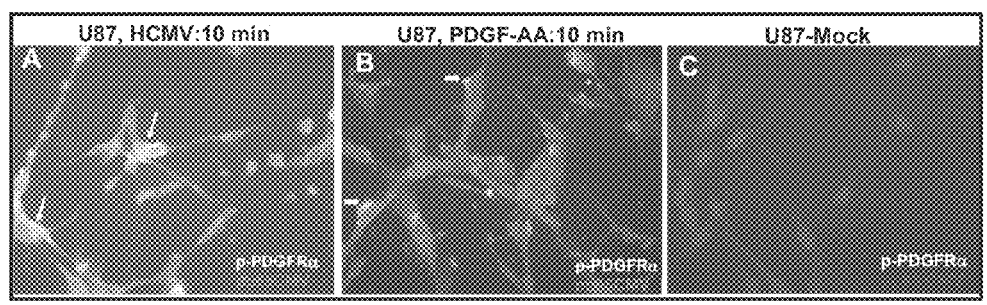
FIG. 15A-C shows that U87 human GBM cells infected with HCMC show phosphorylation of PDGFRα. Immunocytochemical analyses of short term stimulated U87 glioma cells was performed. Double immunofluorescence labeling of U87 human GBM cells demonstrated that HCMV short term treatment induces phosphorylation of PDGFRα in infected cells, similar to the stimulation by genuine ligand, PDGF-AA. (A) HCMV pp65 and p-PDGFRα are detected in the same cells infected by HCMV, (B) p-PDGFRα pattern induced by HCMV infection is comparable to that induced by PDGF-AA treatment; (C) Mock treated cells were negative for both pp65CMV and p-PDGFRα.
Figure 16:
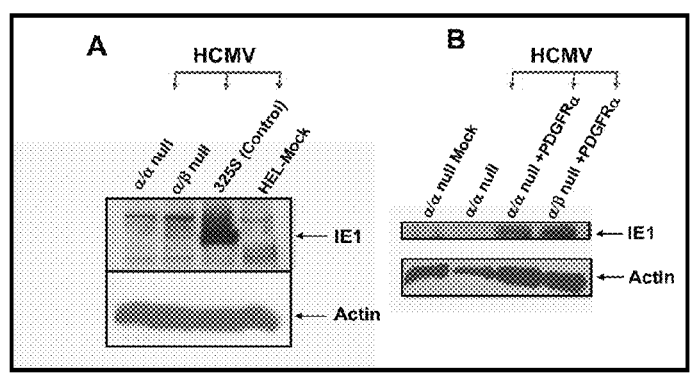
FIG. 16A-B shows HCMV requires PDGFRα for cellular expression of essential viral gene IE1. (A) PDGFRα null mouse fibroblasts and control cells were treated with HCMV or mock infected. Twelve hours following infection, cell lysates were analyzed by Western blot for the presence of IE1 gene product. Only the parental cell line 325S (third lane from the left, upper blot) shows the presence of IE1, while PDGFRα null (a/a null lane) and PDGFRα/β null (α/β null lane) cells do not express IE1, similar to the mock infected cells shown in the lane labeled HEL-Mock. These data supports the notion that PDGFRα is necessary for HCMV infection of mammalian cells. (B) Re-introducing human PDGFRα in α/α null and α/β null fibroblasts restores their susceptibility to HCMV infection.
Figure 17:
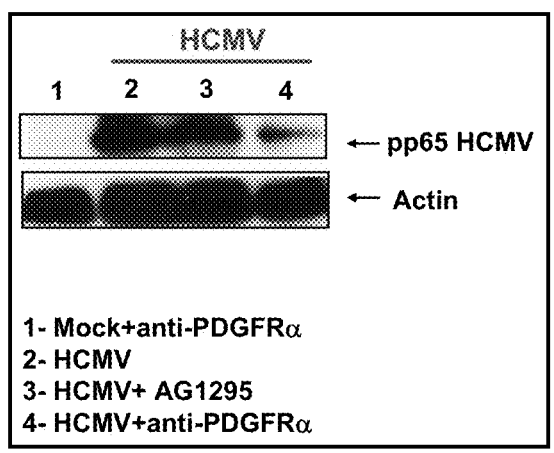
FIG. 17 shows PDGFRα blocking antibody inhibits expression of the HCMV pp65 gene product in HEL cells. Upper panel: HEL cells pretreated with anti-human PDGFRα antibody (10 ng/ml, for 30 min, clone AF-307-NA from R&D; lanes 1 and 4) or with AG 1295 (lane 3, 20 pM, from Calbiochem) were stimulated with Towne HCMV (lanes 2-4) or Mock infected (lane 1) for 10 min at 37 C. Cells were washed and harvested in RIPA buffer and processed for western blotting as described. Upper panel, anti-pp65 blot (1 μg/ml, Novocastra), shows a decrease in the amount of pp65 in the samples treated with inhibitors as compared to control (compare lanes 4 and 2). Lower panel shows loading control western blot for actin (1 μg/ml, from Sigma).
Figure 18:
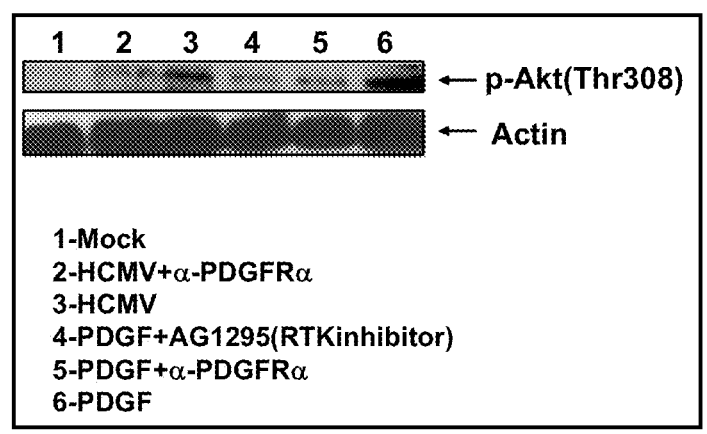
FIG. 18 shows HCMV-induced phosphorylation of Akt is inhibited by anti-PDGFRα blocking antibody. HEL cells pretreated with blocking reagents (as indicated; 30 min, 37 C) were stimulated for 10 min with HCMV, PDGF-AA (5 ng/ml), or mock-treated. Cell lysates were collected in RIPA buffer (supplemented with protease and phosphatase inhibitors) and subjected to Western blot analysis. As shown in the upper panel, p-Akt levels induced by either PDGF or HCMV (lanes 3 and 6) are decreased in the presence of anti-PDGFRα antibody (lanes 5 and 2) and by pre-treatment with AG1925 (lane 4). Actin loading control western blot is shown in the lower panel.
Figure 19:
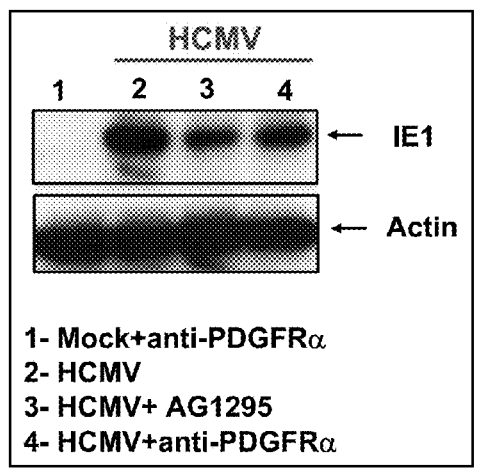
FIG. 19 shows pretreatment with anti-PDGFRα blocking antibody inhibits IE1 expression in HCMV infected cells. Upper panel: HEL cells pretreated with anti-human PDGFRα antibody (10 ng/ml, for 30 min, clone AF-307-NA from R&D; lanes 1 and 3) or with AG 1295 (lane 4, 20 pM, from Calbiochem) were stimulated with Towne HCMV (lanes 2 through 4) or Mock infected (lane 1) for 10 min at 37 C. Cells were washed and further incubated for 2 h at 37 C (to allow expression of IE1 gene product). Afterwards, cells were harvested in RIPA buffer and processed for western blotting as described. Upper panel, anti-IE1 (1 μg/ml, clone MAB 810 from Chemicon), shows a 50% decrease in the amount of IE1 in the sample treated with the blocking antibody as compared to control (compare lanes 3 and 2). Lower panel shows loading control western blot for actin (1 μg/ml, from Sigma).
Figure 20:
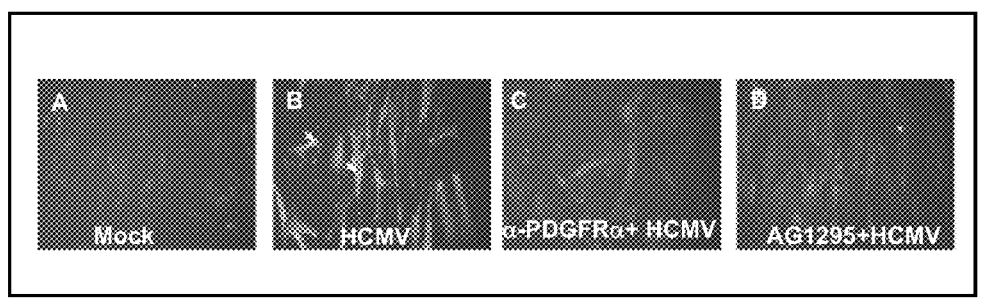
FIG. 20A-D shows pretreatment with PDGFRα Blocking Reagents Inhibits IE1 Gene Expression in Infected HEL cells. Cells were pretreated with anti-PDGFRα neutralizing antibody (panel C) for 1 h or AG1295 Tyrosine kinase inhibitor for 15 min(D) prior to adding HCMV (panels B-D) or Mock (panel A). After 1 h at 37 C, media was replaced and cells were incubated for an additional 6 h. Cells were methanol fixed and stained for IE1 using the MAB810 (Chemicon) in conjunction with Alexa-488 anti mouse secondary antibody. Panels C and D show a significant decrease in IE1 levels in the presence of PDGFRα blocking antibody (from R&D, clone AF-307-NA) or AG1295 kinase inhibitor (from Calbiochem).
Figure 21:
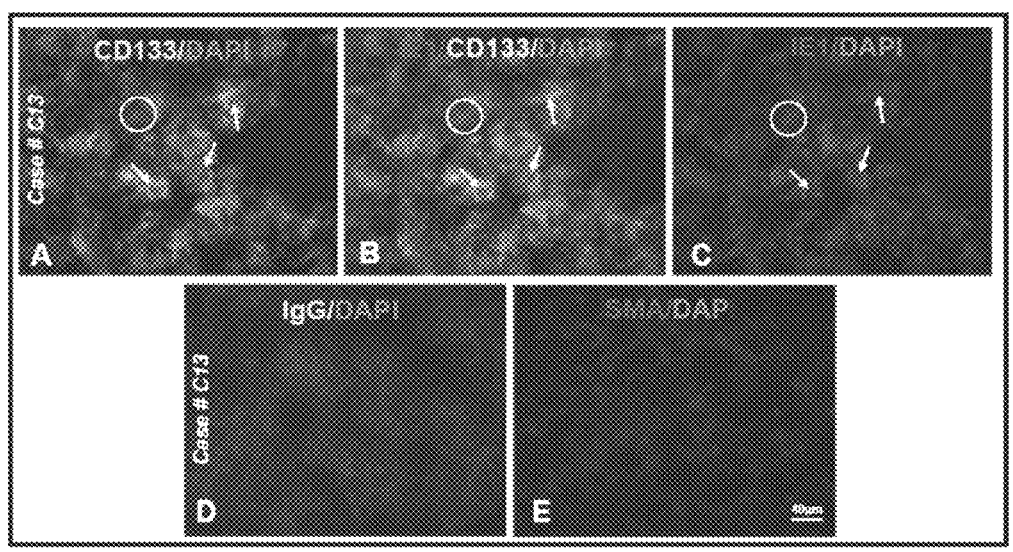
FIG. 21A-E shows double immunofluorescence detection of CD133 and IE1 in a human GBM tissue. 8 μm fresh frozen glioma tissue sections were post-fixed, followed by pepsin digestion for antigen retrieval. For simultaneous detection of IE1 and CD133 the TMR (tetramethylrhodamine)/Fluorescein Tyramide signal amplification system from Perkin Elmer was used. Panel A shows a tissue area with several CD133 positive cells (captured using the FITC filter), while panel C represents the same region captured using a rhodamine fluorescence filter, showing cells positive for IE1. Nuclei are stained with DAPI. Panel B shows superimposed images of from panels A and B. Most IE1 positive cells are also positive for CD133 (arrows); a cell positive only for IE1 is circled in panels A-C. Immunofluorescence labeling of adjacent tissue sections with isotype control antibodies for CD133 (panel D, control IgG from Abcam) and for IE1 (panel E, anti-smooth muscle actin-SMA from Chemicon) and was used to verify specificity of the detection system. Photomicrographs shown in panels A-E were captured using the same exposure times.

Experiments were determined to test whether the authentic PDGFRα ligand inhibits viral entry. Pretreatment with PDGF-AA significantly decreased HCMV entry in HEL cells, suggesting that PDGF-AA competes with an HCMV protein (FIG. 11). Since HCMV envelope glycoprotein B, (gB, UL55) mediates viral entry and cellular signaling, experiments were performed to determine whether gB is the viral moiety directly interacting with PDGFRα. Using a modified attachment assay, results showed that a purified gB peptide was internalized in mouse cells over-expressing hPDGFRα, but not in PDGFRα null cells (FIG. 4a). To demonstrate a direct interaction between PDGFRα and gB, co-immunoprecipitation experiments were performed using HEL cells that endogenously express PDGFRα and purified recombinant full-length gB. Reciprocal immunoblot analyses (FIG. 4b, c) demonstrate that gB and PDGFRα co-immunoprecipitate, indicating direct association between PDGFRα and gB as a bona fide mechanism for attachment/internalization of HCMV into the host cells. Using phosphor-PDGFRα ELISA and western blot approaches, experiments demonstrated that full-length gB induced PDGFRα phosphorylation (FIG. 4d, e). Furthermore, two different gB neutralizing antibodies significantly inhibited HCMV-induced PDGFRα tyrosine phosphorylation (FIG. 4d,e), indicating that the PDGFRα-gB interaction is functionally relevant. Isotype control antibodies or neutralizing antibodies against other viral glycoproteins (gH and gN) did not prevent HCMV-induced receptor activation.

The disclosure demonstrates that HCMV requires PDGFRα binding and activation for viral internalization, expression of essential viral genes, production of infectious virus, and activation of downstream PI3-K/Akt signaling. Viral interaction with PDGFRα is facilitated by direct binding of the viral gB glycoprotein to PDGFRα. In addition, blockade of the PDGFRα receptor pathway with pharmaceutical agents currently in human use provide a powerful antiviral strategy for management of HCMV related disease. Since both PDGFRα and HCMV play important roles in the pathophysiology of human development, inflammation, vascular disease, and cell proliferative disorders, an increased understanding of their interaction may elucidate novel molecular mechanisms underlying these conditions.

What is claimed is:

1. A method for preventing or treating a disease associated with an HCMV infection, comprising contacting a subject with a first agent that inhibits a phosphoinositide 3-kinase, wherein the agent comprises siRNA, and a second agent that blocks PDGFR binding to HCMV, wherein the disease is glioblastoma multiforme.

2. The method of claim 1, wherein HCMV immediate-early 1 gene expression is inhibited by inhibiting phosphoinositide 3-kinase.

3. The method of claim 1, wherein the first agent inhibits the activity of a p110α catalytic subunit of a phosphoinositide 3-kinase.

4. The method of claim 1, wherein the method further comprises administering a small molecule kinase inhibitor.

5. The method of claim 3, wherein the siRNA is against a phosphoinositide 3-kinase p110α catalytic subunit.

6. The method of claim 5, wherein the siRNA comprise two or more sequences having sequences selected from the group consisting of SEQ ID NO:5, 6, 7 and 8.

7. The method of claim 1, wherein the first and second agent are in a composition comprising a pharmaceutically acceptable carrier.

8. The method of claim 1, wherein the second agent inhibits PDGFRα receptor activation.

9. The method of claim 1, wherein second agent is a monoclonal antibody.

10. The method of claim 9, wherein the monoclonal antibody is IMC-3G3.

11. The method of claim 4, wherein the small molecule kinase inhibitor is selected from the group consisting of AZD2171, dasatinib, erlotinib, gefitinib, imatinib, lapatinib, nilotinib, semaxanib, SGI-AXL-277, sunitinib, and vandetanib.

* * * * *

```
                            SEQUENCE LISTING

<160> NUMBER OF SEQ ID NOS: 12

<210> SEQ ID NO 1
<211> LENGTH: 21
<212> TYPE: RNA
<213> ORGANISM: Artificial Sequence
<220> FEATURE:
<223> OTHER INFORMATION: siRNA molecule

<400> SEQUENCE: 1
cgagacuccu guaaccuuau u                                              21

<210> SEQ ID NO 2
<211> LENGTH: 21
<212> TYPE: RNA
<213> ORGANISM: Artificial Sequence
<220> FEATURE:
<223> OTHER INFORMATION: siRNA molecule

<400> SEQUENCE: 2
gagcuucacc uaucaaguuu u                                              21

<210> SEQ ID NO 3
<211> LENGTH: 21
<212> TYPE: RNA
<213> ORGANISM: Artificial Sequence
<220> FEATURE:
<223> OTHER INFORMATION: siRNA molecule

<400> SEQUENCE: 3
gacaguggcc auuauacuau u                                              21

<210> SEQ ID NO 4
<211> LENGTH: 21
<212> TYPE: RNA
<213> ORGANISM: Artificial Sequence
<220> FEATURE:
<223> OTHER INFORMATION: siRNA molecule

<400> SEQUENCE: 4
gaauagggau agcuuccugu u                                              21
```

```
<210> SEQ ID NO 5
<211> LENGTH: 19
<212> TYPE: RNA
<213> ORGANISM: Artificial Sequence
<220> FEATURE:
<223> OTHER INFORMATION: siRNA molecule

<400> SEQUENCE: 5
gcgaaauucu cacacuauu                                                  19

<210> SEQ ID NO 6
<211> LENGTH: 19
<212> TYPE: RNA
<213> ORGANISM: Artificial Sequence
<220> FEATURE:
<223> OTHER INFORMATION: siRNA molecule

<400> SEQUENCE: 6
gugguaaagu ucccagaua                                                  19

<210> SEQ ID NO 7
<211> LENGTH: 19
<212> TYPE: RNA
<213> ORGANISM: Artificial Sequence
<220> FEATURE:
<223> OTHER INFORMATION: siRNA molecule

<400> SEQUENCE: 7
gcuuagaguu ggaguuuga                                                  19

<210> SEQ ID NO 8
<211> LENGTH: 19
<212> TYPE: RNA
<213> ORGANISM: Artificial Sequence
<220> FEATURE:
<223> OTHER INFORMATION: siRNA molecule

<400> SEQUENCE: 8
gacccuagcc uuagauaaa                                                  19

<210> SEQ ID NO 9
<211> LENGTH: 19
<212> TYPE: RNA
<213> ORGANISM: Artificial Sequence
<220> FEATURE:
<223> OTHER INFORMATION: non-targeting RNA molecule

<400> SEQUENCE: 9
ugguuuacua gucgacuaa                                                  19

<210> SEQ ID NO 10
<211> LENGTH: 19
<212> TYPE: RNA
<213> ORGANISM: Artificial Sequence
<220> FEATURE:
<223> OTHER INFORMATION: non-targeting RNA molecule

<400> SEQUENCE: 10
ugguuuacau guuuucuga                                                  19

<210> SEQ ID NO 11
<211> LENGTH: 19
<212> TYPE: RNA
<213> ORGANISM: Artificial Sequence
<220> FEATURE:
<223> OTHER INFORMATION: non-targeting RNA molecule
```

```
<400> SEQUENCE: 11
ugguuuacau guuguguga                                                19

<210> SEQ ID NO 12
<211> LENGTH: 19
<212> TYPE: RNA
<213> ORGANISM: Artificial Sequence
<220> FEATURE:
<223> OTHER INFORMATION: non-targeting RNA molecule

<400> SEQUENCE: 12
ugguuuacau guuuuccua                                                19
```